(12) United States Patent
Lambris et al.

(10) Patent No.: US 10,213,476 B2
(45) Date of Patent: Feb. 26, 2019

(54) COMPSTATIN ANALOGS WITH IMPROVED POTENCY AND PHARMACOKINETIC PROPERTIES

(71) Applicant: The Trustees of the University of Pennsylvania, Philadelphia, PA (US)

(72) Inventors: John D. Lambris, Philadelphia, PA (US); Daniel Ricklin, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/126,937

(22) PCT Filed: Mar. 16, 2015

(86) PCT No.: PCT/US2015/020672
§ 371 (c)(1),
(2) Date: Sep. 16, 2016

(87) PCT Pub. No.: WO2015/142701
PCT Pub. Date: Sep. 24, 2015

(65) Prior Publication Data
US 2017/0173107 A1 Jun. 22, 2017

Related U.S. Application Data

(60) Provisional application No. 61/954,353, filed on Mar. 17, 2014.

(51) Int. Cl.
*C07K 7/08* (2006.01)
*G01N 33/68* (2006.01)
(Continued)

(52) U.S. Cl.
CPC ............ *A61K 38/10* (2013.01); *A61K 47/548* (2017.08); *C07K 7/08* (2013.01); *G01N 33/68* (2013.01);
(Continued)

(58) Field of Classification Search
CPC .......... A61K 38/10; C07K 7/08; C07K 1/107; G01N 33/68; G01N 2440/10; G01N 2500/04
See application file for complete search history.

(56) References Cited

U.S. PATENT DOCUMENTS 4,299,838 A   11/1981   Durlach
4,576,750 A   3/1986    Pitzenberger
(Continued)

FOREIGN PATENT DOCUMENTS

WO   WO2004/026328 A1   4/2004
WO   WO2007/062249 A2   5/2007
(Continued)

OTHER PUBLICATIONS

Aarons, et al., "The binding of ibuprofen to plasma proteins" Eur. J. Clin. Pharmacol. 25:815-818 (1983).
(Continued)

*Primary Examiner* — Jeffrey E. Russel
(74) *Attorney, Agent, or Firm* — Potter Anderson and Corroon, LLP

(57) ABSTRACT

Compounds comprising peptides capable of binding C3 protein and inhibiting complement activation are disclosed. The compounds include a modified compstatin peptide or analog thereof, comprising an added N-terminal component that improves (1) the binding affinity of the peptide to C3, C3b or C3c and/or (2) the plasma stability and/or plasma residence time of the peptide, as compared with an unmodified compstatin peptide under equivalent conditions. Methods of improving the C3 binding of compstatin or compstatin analogs are also disclosed, as well as methods of designing compstatin analogs with improved C3 binding.

3 Claims, 7 Drawing Sheets
Specification includes a Sequence Listing.

(51) Int. Cl.
A61K 38/10 (2006.01)
A61K 47/54 (2017.01)
(52) U.S. Cl.
CPC ..... G01N 2440/10 (2013.01); G01N 2500/04 (2013.01)

(56) References Cited

U.S. PATENT DOCUMENTS

| 4,870,097 A | 9/1989 | Makovec et al. |
| 5,776,970 A | 7/1998 | Shechter et al. |
| 6,169,057 B1 | 1/2001 | Lovatt |
| 6,214,790 B1 | 4/2001 | Richelson et al. |

FOREIGN PATENT DOCUMENTS

| WO | WO2010/127336 A1 | 11/2010 |
| WO | WO2012/040259 A2 | 3/2012 |
| WO | WO2013/036778 A2 | 3/2013 |

OTHER PUBLICATIONS

Amedio Jr., et al., "A Practical Preparation of 4,4-Diphenylcyclohexanol: A Key Intermediate in the Synthesis of Ms-325" Synth. Comm. 28:3895-3906 (1998).
Babitzky & Yanofsky, "Structural Features of L-Tryptophan Required for Activation of TRAP, the trp RNA-binding Attenuation Protein of Bacillus subtilis" J. Biol. Chem. 270:12452-12456 (1995).
Beene, et al., "Cation-p Interaction in Ligand Recognition by Serotonergic (5-HT3A) and Nicotinic Acetylcholine Receptors: The Anomalous Binding Properties of Nicotine", Biochem. 41:10262-10269 (2002).
Caravan, et al., "The Interaction of MS-325 with Human Serum Albumin and Its Effect on Proton Relaxation Rates" J. Am. Chem. Soc. 124:3152-3162 (2002).
Dennis, et al., "Albumin Binding as a General Strategy for Improving the Pharmacokinetics of Proteins" J. Biol. Chem. 277, 35035-35043 (2002).
Dumelin, et al., "A Portable Albumin Binder from a DNA-Encoded Chemical Library" Angew. Chem. Int. Ed. Engl. 47:3196-3201 (2008).
Frimer, et al., "Superoxide Anion Radical (O2-) Mediated Base-Catalyzed Autoxidation of Enones" J. Org. Chem. 54:4853-4866 (1989).
Gao, et al., "Development, Characterization, and Evaluation of a Fusion Protein of a Novel Glucagon-Like Peptide-1 (GLP-1) Analog and Human Serum Albumin in Pichia pastoris" Biosci. Biotechnol. Biochem. 73:688-694 (2009).
Ghuman, et al., "Structural basis of the drug-binding specificity of human serum albumin" J. Mol. Biol. 353:38-52 (2005).
Holers, "The spectrum of complement alternative pathway-mediated disease" Immunol. Rev. 223:300-316 (2008).
Janssen, et al., "Structure of Compstatin in Complex with Complement Component C3c Reveals a New Mechanism of Complement Inhibition" J. Biol. Chem. 282:29241-29247 (2007).
Katragadda & Lambris, "Expression of compstatin in *Escherichia coli*: Incorporation of unnatural amino acids enhances its activity" Protein Expression and Purification 47:289-295 (2006).
Katragadda, et al., "Hydrophobic Effect and Hydrogen Bonds Account for the Improved Activity of a Complement Inhibitor, Compstatin" J. Med. Chem. 49:4616-4622 (2006).
Karlsson, et al., "Analyzing a kinetic titration series using affinity biosensors" Anal. Biochem. 349:136-147 (2006).
Klepeis et al., "Integrated Computational and Experimental Approach for Lead Optimization and Design of Compstatin Variants with Improved Activity" J. Am. Chem. Soc. 125:8422-8423 (2003).
Koehler, et al., "Albumin affinity tags increase peptide half-life in vivo" Bioorg. Med. Chem. Lett. 12:2883-2886 (2002).
Kourtzelis, et al., "Inhibition of biomaterial-induced complement activation attenuates the inflammatory host response to implantation" FASEB J. 27, 2768-2776 (2013).
Kourtzelis, et al., "Complement anaphylatoxin C5a contributes to hemodialysis-associated thrombosis" Blood 116:631-639 (2010).
Kozlowski et al., "Development of Pegylated Interferons for the Treatment of Chronic Hepatitis C" BioDrugs 15:419-429 (2001).
Kratz, "Albumin as a drug carrier: Design of prodrugs, drug conjugates and nanoparticles" J. Control. Release 132:171-183 (2008).
Langenheim & Chen, "Improving the pharmacokinetics/pharmacodynamics of prolactin, GH, and their antagonists by fusion to a synthetic albumin-binding peptide" J. Endocrinol. 203:375-387 (2009).
Lauffer, et al., "MS-325: albumin-targeted contrast agent for MR angiography" Radiology 207:529-538 (1998).
Maekawa, et al., "Genetic and Intervention Studies Implicating Complement C3 as a Major Target for the Treatment of Periodontits" J. Immunol. 192:6020-6027 (2014).
Magotti, et al., "Structure-kinetic relationship analysis of the therapeutic complement inhibitor compstatin" J. Mol. Recognit. 22:495-505 (2009).
Muller, et al., "Physiological Characterization of MS-325 a New Gadolinium Complex, by Multinuclear Relaxometry" Eur. J. Inorg. Chem. 1999:1949-1955 (1999).
Nguyen et al., "the pharmacokinetics of an albumin-binding Fab (AB.Fab) can be modulated as a function of affinity for albumin" Protein Eng. Des. Sel. 19:291-297 (2006).
Pollaro & Heinis, "Strategies to prolong the plasma residence time of peptide drugs" Medchemcomm 1:319-324 (2010).
Qu, et al., "New analogs of the clinical complement inhibitor compstatin with subnanomolar affinity and enhanced pharmacokinetic properties" Immunobiology 218:496-505 (2013).
Qu, et al., "Novel analogues of the therapeutic complement inhibitor compstatin with significantly improved affinity and potency" Mol. Immunol. 48:481-489 (2011).
Qu, et al. "Development of Compstatin Derivative-Albumin Binding Peptide Chimeras for Prolonged Plasma Half-Life" in Proc. Twenty-First Am. Pept. Symp., pp. 219-220 (2009).
Raddatz, et al., "Hydrazide oligonucleotides: new chemical modification for chip array attachment and conjugation" Nucleic Acids Res. 30:4793-4802 (2002).
Ricklin & Lambris, "Complement in immune and inflammatory disorders: therapeutic interventions" J. Immunol. 190:3839-3847 (2013).
Ricklin & Lambris, "Complement in Immune and Inflammatory Disorders: pathophysiological Mechanisms" J. Immunol. 190:3831-3838 (2013).
Ricklin & Lambris, "Compstatin: A Complement Inhibitor on its Way to Clinical Application" in Current Topics in Complement II 632:273-92 (2008).
Risitano, et al., "Peptide inhibitors of C3 activation as a novel strategy of complement inhibition for the treatment of paroxysmal nocturnal hemoglobinuria" Blood 123:2094-2101 (2014).
Robinson, et al., "The design, structures and therapeutic potential of protein epitope mimetics" Drug Disc. Today 13:944-951 (2008).
Sahu, et al., "Inhibition of Human Complement by a C3-Binding Peptide Isolated from a Phage-Displayed Random Peptide Library" J. Immunol. 157:884-891 (1996).
Silasi-Mansat, et al., "Complement inhibition decreases the procoagulant response and confers organ protection in a baboon model of *Escherichia coli* sepsis" Blood 2010, 116, 1002-1010.
Vagner, et al., "Peptidomimetics, a synthetic tool of drug discovery" Curr. Opin. Chem. Biol. 12:292-296 (2008).
Waters, et al., "Validation of a rapid equilibrium dialysis approach for the measurement of plasma binding protein" J. Pharm. Sci. 97:4586-4595 (2008).
Zobel, et al., "Phosphate ester serum albumin affinity tags greatly improve peptide half-life in vivo" Bioorg. Med. Chem. Lett. 13:1513-1515 (2003).
International Search Report and Written Opinion in application No. PCT/US2015/020672, dated Sep. 6, 2015.

COMPSTATIN ANALOGS WITH IMPROVED POTENCY AND PHARMACOKINETIC PROPERTIES

GOVERNMENT SUPPORT

This invention was made with government support under grant numbers AI030040 and AI068730, awarded by National Institute of Health. The government has certain rights in the invention.

FIELD OF THE INVENTION

This invention relates to activation of the complement cascade in the body. In particular, this invention provides compstatin analogs that bind the C3 protein with nanomolar or subnanomolar affinity by virtue of selected N-terminal substituents that target a secondary binding site on C3 and inhibit complement activation. The peptides also exhibit robust plasma stability, albumin binding and resultant in vivo retention.

BACKGROUND OF THE INVENTION

Various publications, including patents, published applications, technical articles and scholarly articles are cited throughout the specification. Each of these cited publications is incorporated by reference herein, in its entirety. Any publication referred to by number in the specification is fully cited at the end of the specification.

Inappropriate or excessive activation of the human complement system is implicated in many clinical disorders.[1] Compstatin, a 13-residue cyclic peptide originally discovered via phage-display library screening (Ile-[Cys-Val-Val-Gln-Asp-Trp-Gly-Ala-His-Arg-Cys]-Thr; cyclic C2-C12; SEQ ID NO:1), interacts with the complement component C3 and its activation fragment C3b, and broadly inhibits complement activation.[2,3] The central role of C3 in complement initiation and amplification pathways renders C3 inhibitors an attractive option for the treatment of a wide range of complement-related conditions, and compstatin analogs have shown promise in disorders ranging from sepsis and biomaterial-induced thromboinflammation to transplantation.[3-6] Whereas an early analog of compstatin (POT-4, Potentia Pharmaceuticals) is in clinical development for the local treatment of age-related macular degeneration, the pharmacokinetic profile of this analog may limit systemic applications. New generations of compstatin derivatives with enhanced inhibitory activity and plasma residence have therefore been developed.[7,8] Backbone N-methylation resulted in analog Cp20 (Ac-Ile-[Cys-Val-Trp(Me)-Gln-Asp-Trp-Sar-Ala-His-Arg-Cys]-mIle-NH$_2$; SEQ ID NO:2) that showed 10-fold improved affinity.[8] Introducing an additional amino acid at the N-terminus of Cp20, thereby extending the target binding site, produced the analog Cp40 ((D)Tyr-Ile-[Cys-Val-Trp(Me)-Gln-Asp-Trp-Sar-Ala-His-Arg-Cys]-mIle-NH$_2$; SEQ ID NO:3) with subnanomolar binding affinity for C3 ($K_D$=0.5 nM). Importantly, pharmacokinetic evaluation in non-human primates (NHP) revealed that these next-generation compstatin analogs follow target-driven elimination kinetics and feature half-life values of up to 12 h, thereby exceeding those typically reported for peptide drugs.[7] Cp40 has shown promise in preclinical models of paroxysmal nocturnal hemoglobinuria and periodontal disease,[9,10] and is currently developed for a variety of systemic disorders.[11] Whereas suitable inhibitor levels for chronic treatment could be achieved via subcutaneous application of Cp40,[9] further extension of its plasma residence is considered beneficial through a decrease in dose intervals.

Among the various strategies to improve the half-life of peptidic drugs, the coupling to albumin-binding tags appears particularly promising.[12] Albumin constitutes ~60% of the total plasma protein pool and has a long circulation residence (t½~20 d); binding to serum albumin has therefore been recognized as an attractive route to extend the plasma residence of biopharmaceuticals.[12,13] Alongside direct coupling approaches,[13,14] several affinity tags based on albumin-binding peptides or molecules (ABP and ABM, respectively) have been developed that allow non-covalent interaction with circulating albumin.[15-19] Chimeras of a compstatin derivative with an ABP have been successfully constructed,[20] yet their synthesis is demanding, given the involvement of two cyclic peptides. Low molecular weight molecules are available. For instance two previously described naphthalene acylsulfonamide[17] and diphenyl-cyclohexanol phosphate ester[18,21] tags have been shown to improve the plasma half-life of therapeutic peptides.[18] One of these tags is being used clinically in the case of MS-325 (gadofosveset trisodium; Ablavar®, Lanteus Medical Imaging), a rationally designed magnetic resonance imaging (MRI) contrast agent with prolonged intravascular half-life (18.5±3 h in human).[21]

In view of the information above, it is clear that a need exists for additional, preferably cost-effective, ways of improving the plasma residence of compstatin and extending its use in systemic indications.

SUMMARY OF THE INVENTION

The present invention provides analogs of the complement-inhibiting peptide, compstatin, which exhibit improved complement-inhibiting activity as compared to even recently developed compstatin analogs, and which also possess improved pharmacokinetic properties resulting from increased plasma residence.

One aspect of the invention features a compound comprising a modified compstatin peptide (ICVVQD-WGHHRCT (cyclic C2-C12; SEQ ID NO:1) or analog thereof, wherein the modification comprises an added N-terminal component that improves (1) the binding affinity of the peptide to C3, C3b or C3c and/or (2) the plasma stability and/or plasma residence time of the peptide, as compared with an unmodified compstatin peptide under equivalent conditions. In certain embodiments, the compound of claim 1, wherein the added component interacts with the C3, C3b or C3c in a shallow groove formed by macroglobulin domain 4 of the C3 β-chain. In particular embodiments, the added component interacts with a secondary binding site involving a lysine residue in C3, C3b or C3c at position at 386 of a C3c sequence comprising SEQ ID NO:5, or equivalent residue thereof in an equivalent sequence of C3, C3b or C3c. In one embodiment, the added component is an albumin-binding compound that also interacts with C3, C3b or C3c. In a particular embodiment, the compound comprises ABM2 linked to the N-terminus of the peptide by an amide linkage.

The aforementioned compound can further comprise additional modifications, including one or more of: replacement of His at position 9 with Ala, replacement of Val at position 4 with Trp or an analog of Trp (such as 1-methyl Trp or 1-formyl Trp), replacement of Trp at position 7 with an analog of Trp (such as a halogenated Trp), modification of Gly at position 8 to constrain the backbone conformation at that location (for instance by replacing the Gly at position 8 (Gly8) with N$^\alpha$-methyl Gly, replacement of Thr at position 13 with Ile, Leu, Nle, N-methyl Thr or N-methyl Ile, replacement of the disulfide bond between C2 and C12 with a thioether bond to form a cystathionine or a lantithionine, replacement of Arg at position 11 with Orn, and/or replacement of Asp at position 6 with Asn.

In certain embodiments, the aforementioned compound is a compstatin analog comprising a peptide having a sequence of SEQ ID NO:6, which is: Xaa1-Cys-Val-Xaa2-Gln-Xaa3-Xaa4-Gly-Xaa5-His-Xaa6-Cys-Xaa7, in which Gly between Xaa4 and Xaa5 optionally is modified to constrain the backbone conformation; wherein: Xaa1 is Ile or Gly; Xaa2 is Trp or an analog of Trp, wherein the analog of Trp has increased hydrophobic character as compared with Trp; Xaa3 is Asp or Asn; Xaa4 is Trp or an analog of Trp comprising a chemical modification to its indole ring wherein the chemical modification increases the hydrogen bond potential of the indole ring; Xaa5 is His, Ala, Phe or Trp; Xaa6 is Arg or Orn; and Xaa7 is Thr, Ile, Leu, Nle, N-methyl Thr or N-methyl Ile, wherein a carboxy terminal —OH of any of the Thr, Ile, Leu, Nle, N-methyl Thr or N-methyl Ile optionally is replaced by —NH$_2$, and the peptide is cyclic via a Cys-Cys or thioether bond. In certain embodiments: the Gly at position 8 is N-methylated; Xaa1 is Ile; Xaa2 is Trp, 1-methyl-Trp or 1-formyl-Trp; Xaa4 is Trp; Xaa5 is Ala; and Xaa7 is Thr, Ile, Leu, Nle, N-methyl Thr or N-methyl Ile with optional replacement of the carboxy terminal —OH with —NH$_2$. In particular, Xaa7 is Ile, N-methyl Thr or N-methyl Ile with optional replacement of the carboxy terminal —OH with —NH$_2$.

The compound of the invention can further comprise an additional component that increases the bioavailability or extends the in vivo retention of the compound. The additional component can be polyethylene glycol (PEG). The additional compound can also be another albumin binding small molecule (ABM) or an albumin binding peptide (ABP) linked to the compound by other than an N-terminal linkage.

Another aspect of the invention features a pharmaceutical composition comprising any of the above-described compounds and a pharmaceutically acceptable carrier. In one embodiment, the pharmaceutical composition is formulated for oral administration. In another embodiment, it is formulated for topical administration. In another embodiment, it is formulated for pulmonary administration. In another embodiment, the pharmaceutical composition is formulated for subcutaneous or intramuscular injection. In another embodiment, it is formulated for intravenous injection or infusion.

Another aspect of the invention provides for the use of any of the above-described compounds for inhibition of complement activation in vivo, ex vivo, in situ or in vitro, as well as for use in the manufacture of a medicament for the inhibition of complement activation.

Another aspect of the invention features a method of improving the C3 binding affinity of compstatin or a compstatin analog, comprising adding an N-terminal component to the compstatin or compstatin analog that improves the binding affinity of the compstatin or compstatin analog to C3, C3b or C3c and, optionally, that improves the plasma stability and/or plasma residence time of the compstatin or compstatin analogy, as compared with an unmodified compstatin or compstatin analog under equivalent conditions. In certain embodiments, the method comprises adding a component that, when N-terminally linked to the compstatin or compstatin analog, interacts with the C3, C3b or C3c in a shallow groove formed by macroglobulin domain 4 of the C3 β-chain. In particular, the method comprises adding a component that, when N-terminally linked to the compstatin or compstatin analog, interacts with a secondary binding site involving a lysine residue in C3, C3b or C3c at position at 386 of a C3c sequence comprising SEQ ID NO:5, or equivalent residue thereof in an equivalent sequence of C3, C3b or C3c. In one embodiment, the added component is an albumin-binding compound that also interacts with C3, C3b or C3c, for instance, ABM2 linked to the N-terminus of the compstatin or compstatin analog, e.g., by an amide linkage in certain embodiments.

Another aspect of the invention features a method of producing a compstatin analog having improved C3 binding affinity. The method comprises (a) constructing a candidate compstatin analog comprising an added N-terminal component designed to interact with, or suspected of interacting with, C3, C3b or C3c in a shallow groove formed by macroglobulin domain 4 of the C3 β-chain; and (b) measuring the binding affinity of the candidate compstatin analog to the C3, C3b or C3c, wherein an increase in the binding affinity indicates that the candidate compstatin analog has improved C3 binding affinity. Confirmatory determinations can be made that the compstatin analog indeed interacts with C3, C3b or C3c at the specified location. In certain embodiments the added N-terminal component interacts with a lysine residue in C3, C3b or C3c at position at 386 of a C3c sequence comprising SEQ ID NO:5, or equivalent residue thereof in an equivalent sequence of C3, C3b or C3c. In certain embodiments, the candidate compstatin analog is also designed to have increased plasma residence time, for instance, by binding albumin. Compstatin analogs produced by the aforementioned method are also featured.

Various features and advantages of the present invention will be understood by reference to the detailed description, drawings and examples that follow.

BRIEF DESCRIPTION OF THE DRAWINGS

FIG. 6. Structure and proposed binding model of ABM2-Cp20.

Figure 1:
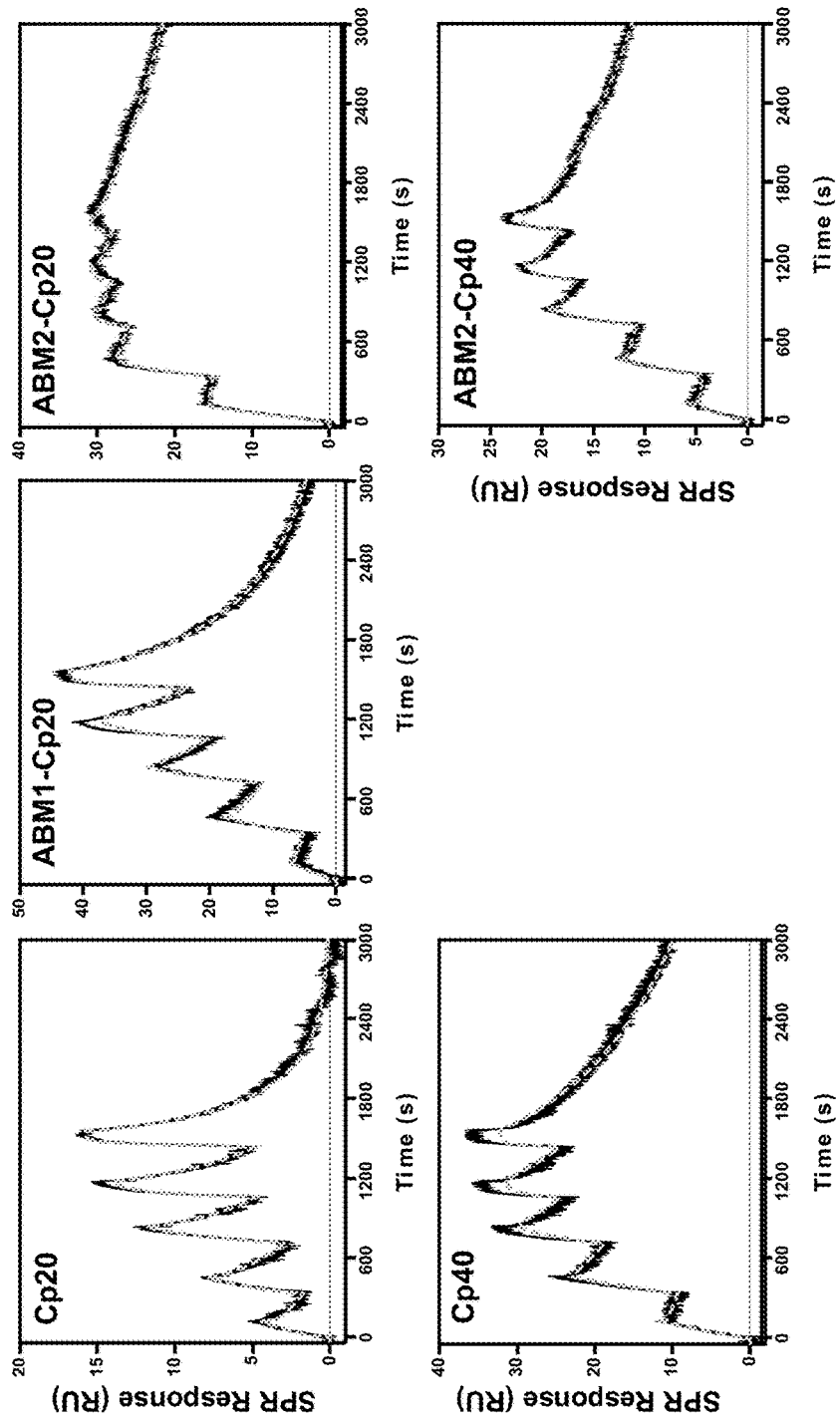
FIG. 1. Kinetic analysis of peptides as listed in Table 1. Each SPR sensorgram represents a representative example of a single cycle kinetic titration of an individual peptide over 5 concentrations. The processed SPR data are shown in one line (dashed, gray line), mostly superimposed on kinetic fit to 1:1 Langmuir model (second line, black).

SEQ ID NO:5 (K386 is shown in bold, underline and capital):

```
  1    spmysiitpn  ilrleseetm  vleandaqgd  vpvtvtvhdf  pgkklvlsse  ktvltpatnh
 61    mgnvtftipa  nrefksekgr  nkfvtvqatf  gtqvvekvvl  vslqsgylfi  qtdktiytpg
121    stvlyriftv  nhkllpvgrt  vmvnienpeg  ipvkqdslss  qnqlgvlpls  wdipelvnmg
181    qwkirayyen  spqqvfstef  evkeyvlpsf  eviveptekf  yyiynekgle  vtitarflyg
241    kkvegtafvi  fgiqdgeqri  slpeslkrip  iedgsgevvl  srkvlldgvq  nlraedlvgk
301    slyvsatvil  hsgsdmvqae  rsgipivtsp  yqihftktpk  yfkpgmpfdl  mvfvtnpdgs
361    payrvpvavq  gedtvqsltq  gdgvaKlsin  thpsqkplsi  tvrtkkqels  eaeqatrtmq
421    alpystvgns  nnylhlsvlr  telrpgetln  vnfllrmdra  heakiryyty  limnkgrllk
481    agrqvrepgq  dlvvlplsit  tdfipsfrlv  ayytligasg  qrevvadsvw  vdvkdscvgs
541    lvvksgqsed  rqpvpgqqmt  lkiegdhgar  vvlvavdkgv  fvlnkknklt  qskiwdvvek
601    adigctpgsg  kdyagvfsda  gltftsssgq  qtaqraelqc  pqp
```

DETAILED DESCRIPTION OF ILLUSTRATIVE EMBODIMENTS

Definitions:

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The following abbreviations may be used herein: Ac, acetyl group; DCM, dichloromethane; DIC, 1,3-diisopropylcarbodiimide; DIPEA, N,N-diisopropylethylamine; DPBS, Dulbecco's Phosphate Buffered Saline; ELISA, enzyme-linked immunosorbent assay; ESI, electrospray ionization; Fmoc, 9-fluorenylmethoxycarbonyl; HOAt, 1-hydroxy-7-aza-benzotriazole; ITC, Isothermal titration calorimetry; MALDI, matrix-assisted laser desorption ionization; MBHA, 4-methylbenzhydrylamine; NMP, N-methylpyrrolidinone; Sar, N-methyl glycine; SPR, surface plasmon resonance; TIPS, triisopropylsilane; Trt, trityl; WFI, water for injection.

The term "about" as used herein when referring to a measurable value such as an amount, a temporal duration, and the like, is meant to encompass variations of ±20% or ±10%, in some embodiments ±5%, in some embodiments ±1%, and in some embodiments ±0.1% from the specified value, as such variations are appropriate to make and used the disclosed compounds and compositions.

The term "compstatin" as used herein refers to a peptide comprising SEQ ID NO:1, ICVVQDWGHHRCT (cyclic C2-C12 by way of a disulfide bond). The term "compstatin analog" refers to a modified compstatin comprising substitutions of natural and/or unnatural amino acids, or amino acid analogs, as well as modifications within or between various amino acids, as described in greater detail herein, and as known in the art. When referring to the location of particular amino acids or analogs within compstatin or compstatin analogs, those locations are sometimes referred to as "positions" within the peptide, with the positions numbered from 1 (Ile in compstatin) to 13 (Thr in compstatin). For example, the Gly residue occupies "position 8."

The term "C3" as used herein refers generally to a two-chain molecule consisting of a β chain (residues 1 to about 645) and an α-chain (residues 650-1,641) of 75 and 110 kDa respectively that are arranged in thirteen domains, whereas C3c consists of three chains: the β-chain (exemplified herein by SEQ ID NO:5) and two fragments of the α-chain, which form ten domains. Activation of C3 occurs by cleavage of the scissile bond Arg-726-Ser-727, generating C3a (9 kDa) and C3b (176 kDa) (Bokisch et al., 1969). The transformation of C3 into C3b induces large conformational changes in the α-chain, but the β-chain is overall structurally stable. Compstatin binds to the β chain at the same location in C3, C3b or C3c (see Ref. 21).

The terms "pharmaceutically active" and "biologically active" refer to the ability of the compounds of the invention to bind C3 or fragments thereof and inhibit complement activation. This biological activity may be measured by one or more of several art-recognized assays, as described in greater detail herein.

As used herein, "alkyl" refers to an optionally substituted saturated straight, branched, or cyclic hydrocarbon having from about 1 to about 10 carbon atoms (and all combinations and subcombinations of ranges and specific numbers of carbon atoms therein), with from about 1 to about 7 carbon atoms being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl. The term "lower alkyl" refers to an optionally substituted saturated straight, branched, or cyclic hydrocarbon having from about 1 to about 5 carbon atoms (and all combinations and subcombinations of ranges and specific numbers of carbon atoms therein). Lower alkyl groups include, but are not limited to, methyl, ethyl, n-propyl, isopropyl, n-butyl, isobutyl, t-butyl, n-pentyl, cyclopentyl, isopentyl and neopentyl.

As used herein, "halo" refers to F, Cl, Br or I.

As used herein, "alkanoyl", which may be used interchangeably with "acyl", refers to an optionally substituted straight or branched aliphatic acylic residue having from about 1 to about 10 carbon atoms (and all combinations and subcombinations of ranges and specific numbers of carbon atoms therein), with from about 1 to about 7 carbon atoms being preferred. Alkanoyl groups include, but are not limited to, formyl, acetyl, propionyl, butyryl, isobutyryl, pentanoyl, isopentanoyl, 2-methyl-butyryl, 2,2-dimethylpropionyl, hexanoyl, heptanoyl, octanoyl, and the like. The term "lower alkanoyl" refers to an optionally substituted straight or branched aliphatic acylic residue having from about 1 to about 5 carbon atoms (and all combinations and subcombinations of ranges and specific numbers of carbon atoms therein. Lower alkanoyl groups include, but are not limited to, formyl, acetyl, n-propionyl, iso-propionyl, butyryl, isobutyryl, pentanoyl, iso-pentanoyl, and the like.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl as defined above, bearing an aryl substituent and having from about 6 to about 20 carbon atoms (and all combinations and subcombinations of ranges and specific numbers of carbon atoms therein), with from about 6 to about 12 carbon atoms being preferred. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy, among others.

As used herein, "carboxy" refers to a —C(=O)OH group.

As used herein, "alkoxycarbonyl" refers to a —C(=O) O-alkyl group, where alkyl is as previously defined.

As used herein, "aroyl" refers to a —C(=O)-aryl group, wherein aryl is as previously defined. Exemplary aroyl groups include benzoyl and naphthoyl.

Typically, substituted chemical moieties include one or more substituents that replace hydrogen at selected locations on a molecule. Exemplary substituents include, for example, halo, alkyl, cycloalkyl, aralkyl, aryl, sulfhydryl, hydroxyl (—OH), alkoxyl, cyano (—CN), carboxyl (—COOH), acyl (alkanoyl: —C(=O)R); —C(=O)O-alkyl, aminocarbonyl (—C(=O)NH$_2$), —N-substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term D-amino acid" refers to dextrorotatory alpha-amino acids. Unless specified otherwise, all amino acids referred to herein are L-amino acids.

"Hydrophobic" or "nonpolar" are used synonymously herein, and refer to any inter- or intra-molecular interaction not characterized by a dipole.

"PEGylation" refers to the reaction in which at least one polyethylene glycol (PEG) moiety, regardless of size, is chemically attached to a protein or peptide to form a PEG-peptide conjugate. "PEGylated means that at least one PEG moiety, regardless of size, is chemically attached to a peptide or protein. The term PEG is generally accompanied by a numeric suffix that indicates the approximate average molecular weight of the PEG polymers; for example, PEG-8,000 refers to polyethylene glycol having an average molecular weight of about 8,000 Daltons (or g/mol).

As used herein, "pharmaceutically acceptable salts" refers to derivatives of the disclosed compounds wherein the parent compound is modified by making acid or base salts thereof. Examples of pharmaceutically-acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds of the present invention may exist as zwitterions. All forms of the compounds, including free acid, free base, and zwitterions, are contemplated to be within the scope of the present invention.

Description:

The present invention springs in part from the inventors' discovery of an additional compstatin binding location on C3, accessible by way of certain N-terminal modifications on compstatin. The newly-identified binding site is located in a shallow groove formed by macroglobulin domain 4 of the C3 β-chain, in particular at a lysine residue at position 386 of the β-chain (numbering referring to a C3c sequence comprising SEQ ID NO:5).

In an exemplary embodiment, conjugates of compstatin analogs and albumin-binding molecules (ABM) to increase circulatory residence were also found to have increased binding affinity for C3 as compared with an unmodified counterpart.

Reference is made to the exemplary analog set forth below, ABM2-Cp20 (SEQ ID NO:4), which show significantly improved activity and/or affinity over its unmodified counterpart, Cp20 (SEQ ID NO:2).

"ABM2-Compstatin 20" (ABM2-Cp20) (SEQ ID NO:4):

ABM2-Ile-[Cys-Val-Trp(Me)-Gln-Asp-Trp-Sar-Ala-His-Arg-Cys]-mIle-NH$_2$

Without intending to be bound or limited by theory, it is believed that the improved C3 binding affinity of the analogs described herein is due at least in part to higher binding affinity as a consequence of interactions between the N-terminal component and the newly identified binding location described above. As described in detail in Example 2, ABM2-Cp20 was found to participate in hydrogen bonding at the specified location via the phosphate substituent on the N-terminal ABM2 component.

The above-described N-terminal modifications can be combined with other modifications of compstatin previously shown to improve activity, thereby producing peptides with significantly improved complement inhibiting activity. For example, it is known that substitution of Ala for His at position 9 improves activity of compstatin and is a preferred modification of the peptides of the present invention as well. It has also been determined that substitution of Tyr for Val at position 4 can result in a modest improvement in activity (Klepeis et al., 2003, *J Am Chem Soc* 125: 8422-8423).

It was disclosed in WO2004/026328 and WO2007/0622249 that Trp and certain Trp analogs at position 4, as well as certain Trp analogs at position 7, especially combined with Ala at position 9, yields many-fold greater activity than that of compstatin. These modifications are used to advantage in the present invention as well.

In particular, peptides comprising 5-fluoro-tryptophan or either 5-methoxy-, 5-methyl- or 1-methyl-tryptophan, or 1-formyl-tryptophan at position 4 have been shown to possess 31-264-fold greater activity than compstatin. Particularly preferred are 1-methyl and 1-formyl tryptophan. It is believed that an indole 'N'-mediated hydrogen bond is not necessary at position 4 for the binding and activity of compstatin. The absence of this hydrogen bond or reduction of the polar character by replacing hydrogen with lower alkyl, alkanoyl or indole nitrogen at position 4 enhances the binding and activity of compstatin. Without intending to be limited to any particular theory or mechanism of action, it is believed that a hydrophobic interaction or effect at position 4 strengthens the interaction of compstatin with C3. Accordingly, modifications of Trp at position 4 (e.g., altering the structure of the side chain according to methods well known in the art), or substitutions at position 4 or position 7 of Trp analogs that maintain or enhance the aforementioned hydrophobic interaction are contemplated in the present invention as an advantageous modification in combination with the modifications at positions 8 and 13 as described above. Such analogs are well known in the art and include, but are not limited to the analogs exemplified herein, as well as unsubstituted or alternatively substituted derivatives thereof. Examples of suitable analogs may be found by reference to the following publications, and many others: Beene, et al., 2002, *Biochemistry* 41: 10262-10269 (describing, inter alia, singly- and multiply-halogenated Trp analogs); Babitzky & Yanofsky, 1995, *J. Biol. Chem.* 270: 12452-12456 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Trp analogs may be introduced into the compstatin peptide by in vitro or in vivo expression, or by peptide synthesis, as known in the art.

In certain embodiments, Trp at position 4 of compstatin is replaced with an analog comprising a 1-alkyl substituent, more particularly a lower alkyl (e.g., $C_1$-$C_5$) substituent as defined above. These include, but are not limited to, N($\alpha$) methyl tryptophan and 5-methyltryptophan. In other embodiments, Trp at position 4 of compstatin is replaced with an analog comprising a 1-alkanoyl substituent, more particularly a lower alkanoyl (e.g., $C_1$-$C_5$) substituent as defined above, e.g., N($\alpha$) formyl tryptophan, 1-acetyl-L-tryptophan and L-$\beta$-homotryptophan.

It was disclosed in WO2007/0622249 that incorporation of 5-fluoro-tryptophan at position 7 in compstatin increased the enthalpy of the interaction between the resulting compstatin analog and C3, relative to compstatin, whereas incorporation of 5-fluoro-tryptophan at position 4 in decreased the enthalpy of this interaction. Accordingly, modifications of Trp at position 7, as described in WO2007/0622249, are contemplated as useful modifications in combination with the N-terminal modifications described above.

Other modifications are described in WO2010/127336. One modification disclosed in that document comprises constraint of the peptide backbone at position 8 of the peptide. In a particular embodiment, the backbone is constrained by replacing glycine at position 8 ($Gly^8$) with N-methyl glycine. Another modification disclosed in that document comprises replacing Thr at position 13 with Ile, Leu, Nle (norleucine), N-methyl Thr or N-methyl Ile.

Still other modifications are described in WO2012/040259. One such modification comprises replacement of the C2-C12 disulfide bond with addition of a $CH_2$ to form a homocysteine at C2 or C12, and introduction of a thioether bond, to form a cystathionine, such as a gamma-cystathionine or a delta-cystathionine. Another modification comprises replacement of the C2-C12 disulfide bond with a thioether bond without the addition of a $CH_2$, thereby forming a lantithionine. The analogs comprising the thioether bond demonstrate activity that is substantially the same as that of certain of the disulfide bond analogs and also possess equivalent or improved stability characteristics.

Yet other internal modifications are described in WO2013/036778. For instance, substituting ornithine for arginine at position 11, and/or substituting asparagine for aspartic acid at position 6 of certain compstatin analogs, results in analogs with binding and complement inhibitory activity similar to the parent compounds. In addition, one or both of those substitutions is expected to render the analogs less susceptible to metabolism by certain physiological enzymes found in the intestinal tract, liver or plasma.

The modified compstatin peptides of the present invention may be prepared by various synthetic methods of peptide synthesis via condensation of one or more amino acid residues, in accordance with conventional peptide synthesis methods. For example, peptides are synthesized according to standard solid-phase methodologies. Other methods of synthesizing peptides or peptidomimetics, either by solid phase methodologies or in liquid phase, are well known to those skilled in the art. During the course of peptide synthesis, branched chain amino and carboxyl groups may be protected/deprotected as needed, using commonly known protecting groups. An example of a suitable peptide synthetic method is set forth in Example 1. Modification utilizing alternative protecting groups for peptides and peptide derivatives will be apparent to those of skill in the art.

Alternatively, peptides may be produced at least in part by expression in a suitable prokaryotic or eukaryotic system. For example, a DNA construct may be inserted into a plasmid vector adapted for expression in a bacterial cell (such as *E. coli*) or a yeast cell (such as *Saccharomyces cerevisiae*), or into a baculovirus vector for expression in an insect cell or a viral vector for expression in a mammalian cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The peptides can also be produced by expression of a nucleic acid molecule in vitro or in vivo. A DNA construct encoding a concatemer of the peptides, the upper limit of the concatemer being dependent on the expression system utilized, may be introduced into an in vivo expression system. After the concatemer is produced, cleavage between the C-terminal Asn and the following N-terminal G is accomplished by exposure of the polypeptide to hydrazine.

The peptides produced by gene expression in a recombinant prokaryotic or eucaryotic system may be purified according to methods known in the art. A combination of gene expression and synthetic methods may also be utilized to produce compstatin analogs. For example, an analog can be produced by gene expression and thereafter subjected to one or more post-translational synthetic processes, e.g., to modify the N- or C-terminus or to cyclize the molecule.

Advantageously, peptides that incorporate unnatural amino acids, e.g., methylated amino acids, may be produced by in vivo expression in a suitable prokaryotic or eukaryotic system. For example, methods such as those described by Katragadda & Lambris (2006, Protein Expression and Purification 47: 289-295) to introduce unnatural Trp analogs into compstatin via expression in *E. coli* auxotrophs may be utilized to introduce N-methylated or other unnatural amino acids at selected positions of compstatin.

The structure of compstatin is known in the art, and the structures of the foregoing analogs are determined by similar means. Once a particular desired conformation of a short peptide has been ascertained, methods for designing a peptide or peptidomimetic to fit that conformation are well known in the art. Of particular relevance to the present invention, the design of peptide analogs may be further refined by considering the contribution of various side chains of amino acid residues, as discussed above (i.e., for the effect of functional groups or for steric considerations).

It will be appreciated by those of skill in the art that a peptide mimic may serve equally well as a peptide for providing the specific backbone conformation and side chain functionalities required for binding to C3 and inhibiting complement activation. Accordingly, it is contemplated as being within the scope of the present invention to produce C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of the peptides of the invention, which possess the same backbone conformational features and/or other functionalities, so as to be sufficiently similar to the exemplified peptides to inhibit complement activation.

The use of peptidomimetics for the development of high-affinity peptide analogs is well known in the art (see, e.g., Vagner et al., 2008, *Curr. Opin. Chem. Biol.* 12: 292-296; Robinson et al., 2008, *Drug Disc. Today* 13: 944-951) Assuming rotational constraints similar to those of amino acid residues within a peptide, analogs comprising non-amino acid moieties may be analyzed, and their conformational motifs verified, by any variety of computational techniques that are well known in the art.

The modified compstatin peptides of the present invention can be modified by the addition of polyethylene glycol (PEG) components to the peptide. As is well known in the art, PEGylation can increase the half-life of therapeutic peptides and proteins in vivo. In one embodiment, the PEG has an average molecular weight of about 1,000 to about 50,000. In another embodiment, the PEG has an average molecular weight of about 1,000 to about 20,000. In another embodiment, the PEG has an average molecular weight of about 1,000 to about 10,000. In an exemplary embodiment, the PEG has an average molecular weight of about 5,000. The polyethylene glycol may be a branched or straight chain, and preferably is a straight chain.

The compstatin analogs of the present invention can be covalently bonded to PEG via a linking group. Such methods are well known in the art. (Reviewed in Kozlowski A. et al. 2001, *BioDrugs* 15: 419-29; see also, Harris J M and Zalipsky S, eds. Poly(ethylene glycol), Chemistry and Biological Applications, ACS Symposium Series 680 (1997)). Non-limiting examples of acceptable linking groups include an ester group, an amide group, an imide group, a carbamate group, a carboxyl group, a hydroxyl group, a carbohydrate, a succinimide group (including without limitation, succinimidyl succinate (SS), succinimidyl propionate (SPA), succinimidyl carboxymethylate (SCM), succinimidyl succinamide (SSA) and N-hydroxy succinimide (NHS)), an epoxide group, an oxycarbonylimidazole group (including without limitation, carbonyldimidazole (CDI)), a nitro phenyl group (including without limitation, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine. In certain embodiments, the linking group is a succinimide group. In one embodiment, the linking group is NHS.

The compstatin analogs of the present invention can alternatively be coupled directly to PEG (i.e., without a linking group) through an amino group, a sulfhydryl group, a hydroxyl group or a carboxyl group. In one embodiment, PEG is coupled to a lysine residue added to the C-terminus of compstatin.

As an alternative to PEGylation, the in vivo clearance of peptides can also be reduced by linking the peptides to certain other molecules or peptides. For instance, certain albumin binding peptides (ABP) display an unusually long half-life of 2.3 h when injected by intravenous bolus into rabbits (Dennis et al., 2002, *J Biol Chem.* 277: 35035-35043). A peptide of this type, fused to the anti-tissue factor Fab of D3H44 enabled the Fab to bind albumin while retaining the ability of the Fab to bind tissue factor (Nguyen et al., 2006, *Protein Eng Des Sel.* 19: 291-297.). This interaction with albumin resulted in significantly reduced in vivo clearance and extended half-life in mice and rabbits, when compared with the wild-type D3H44 Fab, comparable with those seen for PEGylated Fab molecules, immunoadhesins, and albumin fusions. WO2010/127336 sets forth suitable synthesis strategies utilizing an ABP, as well as ABMs, which can be linked to the C-terminus of the peptide so as to avoid interference with the N-terminal interactions described herein.

The complement activation-inhibiting activity of compstatin analogs, peptidomimetics and conjugates may be tested by a variety of assays known in the art. In certain embodiments, the assays described in the Examples are utilized. A non-exhaustive list of other assays is set forth in WO2004/026328, WO2007/062249, WO2010/127336, WO2012/040259 and WO2013/036778, including, but not limited to, (1) peptide binding to C3 and C3 fragments; (2) various hemolytic assays; (3) measurement of C3 convertase-mediated cleavage of C3; and (4) measurement of Factor B cleavage by Factor D.

The peptides and peptidomimetics described herein are of practical utility for any purpose for which compstatin itself is utilized, as known in the art. Such uses include, but are not limited to: (1) inhibiting complement activation in the blood or serum, and on cells, tissues or organs of a patient (human or animal), which can facilitate treatment of certain diseases or conditions, including but not limited to, age-related macular degeneration, rheumatoid arthritis, spinal cord injury, Parkinson's disease, Alzheimer's disease, cancer, sepsis, paroxysmal nocturnal hemoglobinuria, psoriasis and respiratory disorders such as asthma, chronic obstructive pulmonary disease (COPD), allergic inflammation, emphysema, bronchitis, bronchiecstasis, cystic fibrosis, tuberculosis, pneumonia, respiratory distress syndrome (RDS—neonatal and adult), rhinitis and sinusitis; (2) inhibiting complement activation that occurs during cell or organ transplantation, or in the use of artificial organs or implants (e.g., by time-restricted systemic administration before, during and/or after the procedure or by coating or otherwise treating the cells, organs, artificial organs or implants with a peptide of the invention); (3) inhibiting complement activation that occurs during extracorporeal shunting of physiological fluids (blood, urine) (e.g., by time-restricted systemic administration before, during and/or after the procedure or by coating the tubing through which the fluids are shunted with a peptide of the invention); and (4) in screening of peptide or small molecule libraries to identify other inhibitors of compstatin activation (e.g., liquid- or solid-phase high-throughput assays designed to measure the ability of a test compound to compete with a compstatin analog for binding with C3 or a C3 fragment).

To implement one or more of the utilities mentioned above, another aspect of the invention features pharmaceutical compositions comprising the compstatin analogs or conjugates described and exemplified herein. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

A particular compstatin analog of the invention may be selected for a particular formulation on the basis of its solubility characteristics. As mentioned above, analogs that are highly soluble in water or buffered saline may be particularly suitable for systemic injection because the injection volume can be minimized. By comparison, analogs with high water solubility and lower solubility in buffered saline could produce a more long-lasting gel, suspension or precipitate for topical application or local injection, such as intraocular injection.

The formulations of the pharmaceutical compositions may be prepared by any method known or hereafter developed in the art of pharmaceutical technology. In general, such preparatory methods include the step of bringing the active ingredient into association with a carrier or one or more other accessory ingredients, and then, if necessary or desirable, shaping or packaging the product into a desired single- or multi-does unit.

As used herein, the term "pharmaceutically-acceptable carrier" means a chemical composition with which a compstatin analog may be combined and which, following the combination, can be used to administer the compstatin analog to an individual.

As used herein, the term "physiologically acceptable" ester or salt means an ester or salt form of the active ingredient which is compatible with any other ingredients of the pharmaceutical composition, which is not deleterious to the subject to which the composition is to be administered.

The pharmaceutical compositions useful for practicing the invention may be administered to deliver a dose of between 1 ng/kg and 100 mg/kg body weight as a single bolus, or in a repeated regimen, or a combination thereof as readily determined by the skilled artisan. In certain embodiments, the dosage comprises at least 0.1 mg/kg, or at least 0.2 mg/kg, or at least 0.3 mg/kg, or at least 0.4 mg/kg, or at least 0.5 mg/kg, or at least 0.6 mg/kg, or at least 0.7 mg/kg, or at least 0.8 mg/kg, or at least 0.9 mg/kg, or at least 1 mg/kg, or at least 2 mg/kg, or at least 3 mg/kg, or at least 4 mg/kg, or at least 5 mg/kg, or at least 6 mg/kg, or at least 7 mg/kg, or at least 8 mg/kg, or at least 9 mg/kg, or at least 10 mg/kg, or at least 15 mg/kg, or at least 20 mg/kg, or at least 25 mg/kg, or at least 30 mg/kg, or at least 35 mg/kg, or at least 40 mg/kg, or at least 45 mg/kg, or at least 50 mg/kg, or at least 55 mg/kg, or at least 60 mg/kg, or at least 65 mg/kg, or at least 70 mg/kg, or at least 75 mg/kg, or at least 80 mg/kg, or at least 85 mg/kg, or at least 90 mg/kg, or at least 95 mg/kg, or at least 100 mg/kg, on a daily basis or on another suitable periodic regimen. In a particular embodiment, the dosage is between about 0.5 mg/kg and about 20 mg/kg, or between about 1 mg/kg and about 10 mg/kg, or between about 2 mg/kg and about 6 mg/kg.

In one embodiment, the invention envisions administration of a dose that results in a serum concentration of the compstatin analog between about 0.01 µM and about 30 µM in an individual. In certain embodiments, the combined dose and regimen will result in a serum concentration, or an average serum concentration over time, of the compstatin analog of at least about 0.01 µM, or at least about 0.02 µM, or at least about 0.03 µM, or at least about 0.04 µM, or at least about 0.05 µM, or at least about 0.06 µM, or at least about 0.07 µM, or at least about 0.08 µM, or at least about 0.09 µM, or at least about 0.1 µM, 0.11 µM, or at least about 0.12 µM, or at least about 0.13 µM, or at least about 0.14 µM, or at least about 0.15 µM, or at least about 0.16 µM, or at least about 0.17 µM, or at least about 0.18 µM, or at least about 0.19 µM, or at least about 0.2 µM, or at least about 0.3 µM, or at least about 0.4 µM, or at least about 0.5 µM, or at least about 0.6 µM, or at least about 0.7 µM, or at least about 0.8 µM, or at least about 0.9 µM, or at least about 1 µM or at least about 1.5 µM, or at least about 2 µM, or at least about 2.5 µM, or at least about 3 µM, or at least about 3.5 µM, or at least about 4 µM, or at least about 4.5 µM, or at least about 5 µM, or at least about 5.5 µM, or at least about 6 µM, or at least about 6.5 µM, or at least about 7 µM, or at least about 7.5 µM, or at least about 8 µM, or at least about 8.5 µM, or at least about 9 µM, or at least about 9.5 µM, or at least about 10 µM, or at least about 10.5 µM, or at least about 11 µM or at least about 11.5 µM, or at least about 12 µM, or at least about 12.5 µM, or at least about 13 µM, or at least about 13.5 µM, or at least about 14 µM, or at least about 14.5 µM, or at least about 15 µM, or at least about 15.5 µM, or at least about 16 µM, or at least about 16.5 µM, or at least about 17 µM, or at least about 17.5 µM, or at least about 18 µM, or at least about 18.5 µM, or at least about 19 µM, or at least about 19.5 µM, or at least about 20 µM, or at least about 20.5 µM, or at least about 21 µM or at least about 21.5 µM, or at least about 22 µM, or at least about 22.5 µM, or at least about 23 µM, or at least about 23.5 µM, or at least about 24 µM, or at least about 24.5 µM, or at least about 25 µM, or at least about 25.5 µM, or at least about 26 µM, or at least about 26.5 µM, or at least about 27 µM, or at least about 27.5 µM, or at least about 28 µM, or at least about 28.5 µM, or at least about 29 µM, or at least about 29.5 µM, or at least about 30 µM. In certain embodiments, the combined dose and regimen will result in a serum concentration, or an average serum concentration over time, of the compstatin analog of up to about 0.1 µM, or up to about 0.11 µM, or up to about 0.12 µM, or up to about 0.13 µM, or up to about 0.14 µM, or up to about 0.15 µM, or up to about 0.16 µM, or up to about 0.17 µM, or up to about 0.18 µM, or up to about 0.19 µM, or up to about 0.2 µM, or up to about 0.3 µM, or up to about 0.4 µM, or up to about 0.5 µM, or up to about 0.6 µM, or up to about 0.7 µM, or up to about 0.8 µM, or up to about 0.9 µM, or up to about 1 µM or up to about 1.5 µM, or up to about 2 µM, or up to about 2.5 µM, or up to about 3 µM, or up to about 3.5 µM, or up to about 4 µM, or up to about 4.5 µM, or up to about 5 µM, or up to about 5.5 µM, or up to about 6 µM, or up to about 6.5 µM, or up to about 7 µM, or up to about 7.5 µM, or up to about 8 µM, or up to about 8.5 µM, or up to about 9 µM, or up to about 9.5 µM, or up to about 10 µM, or up to about 10.5 µM or up to about 11 µM or up to about 11.5 µM, or up to about 12 µM, or up to about 12.5 µM, or up to about 13 µM, or up to about 13.5 µM, or up to about 14 µM, or up to about 14.5 µM, or up to about 15 µM, or up to about 15.5 µM, or up to about 16 µM, or up to about 16.5 µM, or up to about 17 µM, or up to about 17.5 µM, or up to about 18 µM, or up to about 18.5 µM, or up to about 19 µM, or up to about 19.5 µM, or up to about 20 µM, or up to about 20.5 µM or up to about 21 µM or up to about 21.5 µM, or up to about 22 µM, or up to about 22.5 µM, or up to about 23 µM, or up to about 23.5 µM, or up to about 24 µM, or up to about 24.5 µM, or up to about 25 µM, or up to about 25.5 µM, or up to about 26 µM, or up to about 26.5 µM, or up to about 27 µM, or up to about 27.5 µM, or up to about 28 µM, or up to about 28.5 µM, or up to about 29 µM, or up to about 29.5 µM, or up to about 20 µM.

Suitable ranges include about 0.1 to about 30 µM, or about 1 to about 29 µM, or about 2 to about 28 µM, or about 3 to about 27 µM, or about 4 to about 26 µM, or about 5 to about 25 µM, or about 6 to about 24 µM, or about 7 to about 23 µM, or about 8 to about 22 µM, or about 9 to about 21 µM, or about 10 to about 20 µM, or about 11 to about 19 µM, or about 12 to about 18 µM, or about 13 to about 17 µM, or about 1 to about 5 µM, or about 5 to about 10 µM, or about 10 to about 15 µM, or about 15 to about 20 µM, or about 20 to about 25 µM, or about 25 to about 30 µM. While the precise dosage administered will vary depending upon any number of factors, including but not limited to, the type of patient and type of disease state being treated, the age of the patient and the route of administration, such dosage is readily determinable by the person of skill in the art.

The pharmaceutical composition can be administered to a patient as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the patient, as described above.

Pharmaceutical compositions that are useful in the methods of the invention may be administered systemically in oral, parenteral, ophthalmic (including intravitreal), suppository, aerosol, topical, transdermal or other similar formulations. Such pharmaceutical compositions may contain pharmaceutically acceptable carriers and other ingredients known to enhance and facilitate drug administration. Other formulations, such as nanoparticles, liposomes, resealed erythrocytes, and immunologically based systems may also be used to administer a compstatin analog according to the methods of the invention.

As used herein, "oral administration" or "enteral administration" of a pharmaceutical composition includes any route of administration characterized by introduction into the gastrointestinal tract. Such administration includes feeding by mouth as well as orogastric or intragastric gavage. Such administration also may include sublingual, buccal, intranasal, pulmonary or rectal administration, among other routes known in the art.

Formulations of a pharmaceutical composition suitable for oral administration comprise the active ingredient combined with a pharmaceutically acceptable carrier, in a variety of dosage forms, including but not limited to pills, tablets, granules, powders, capsules, dispersions, suspensions, solutions, emulsions, microemulsions, gels and films, to name a few. Such dosage forms typically include carriers and excipients to facilitate formulation and delivery of the active ingredients.

The pharmaceutically acceptable carriers are selected from proteins, carbohydrates, lipids, organic and inorganic molecules, and combinations thereof. The active ingredients can be combined with the carrier in an appropriate diluent to form a solution or a suspension. Such liquid formulations can be viscous or non-viscous depending on the amount and the carrier used. The liquid formulations can be used directly or can be further formulated into an appropriate capsule, gel capsule or solid by methods know to those skilled in the art. Alternatively, solid formulations can be made by combining solid components. Such solid formulations can be used as a powder or formulated into granules, capsules, tablets or films any one of which can be made as a time release formulation.

Suitable proteins for use as carriers in oral dosage forms include milk proteins such as casein, sodium caseinate, whey, reduced lactose whey, whey protein concentrate, gelatin, soy protein (isolated), brown algae protein, red algae protein, baker's yeast extract and albumins. Suitable carbohydrates include celluloses such as methylcellulose, sodium carboxymethylcellulose, carboxymethylcellulose, hydroxypropylcellulose, hydroxypropylmethylcellulose, cellulose acetate and ethyl cellulose, starches such as cornstarch, potato starch, tapioca starch, wheat starch, acid modified starch, pregelatinized starch and unmodified starch, alginates such as ammonium alginate, sodium alginate, and calcium alginate, glutens such as corn gluten and wheat gluten, gums such as acacia (gum Arabic), gum ghatti, guar gum, karaya gum (sterculia gum) and gum (tragacanth), insoluble glucose isomerase enzyme preparations, sugars such as corn sugar, invert sugar, corn syrup, high fructose corn syrup, and sodium gluconate. Suitable lipids include tocopherols such as a-tocopherol acetate, short-, medium- and long-chain fatty acids and esters thereof, fatty alcohols and ethers thereof, oils such as coconut oil (refined), soybean oil (hydrogenated) and rapeseed oil, aluminum palmitate, dilauryl thiodipropionate, enzyme-modified lecithin, calcium stearate, enzyme-modified fats, glyceryl palmitostereate, lecithin, mono- and diglycerides, glycerin and waxes such as beeswax (yellow and white), candelilla wax and carnauba wax and vegetable oil. Suitable organic and inorganic substances include methyl and vinyl pyrrolidones such as polyvinylpyrrolidone, methylsulfonyl methane, dimethylsulfoxide and related compounds, hydroxy and polyhydroxy acids such as polylactic acid, among many others.

In some embodiments, controlled release forms may be prepared to achieve a sustained, or location-specific liberation of the compstatin analog in the digestive tract in order to improve absorption and prevent certain forms of metabolism. For example, acid-resistant coatings of tablet or acid-resistant capsule materials may be used to prevent a release of compstatin analogs in the stomach and protect the compound from metabolism by gastric enzymes. Suitable materials and coatings to achieve controlled release after passage of the stomach are primarily composed of fatty acids, waxes, shellac, plastics and plant fibers and include, but are not limited to, methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate, sodium alginate or stearic acid. Sustained release in the gastrointestinal tract can for example be achieved by embedding compstatin analogs in a matrix of insoluble substances such as various acrylics, chitin and others. Methods to prepare such formulations are known to those skilled in the art.

Compstatin may be formulated into suppositories or clysters for rectal, vaginal or urethral administration. For this purpose, compstatin analogs can be dissolved or suspended in a greasy base carrier such as cocoa butter that is solid or semi-solid at room temperature but melts at body temperature or in a water-soluble solid base such as polyethylene glycol or glycerin (made from glycerol and gelatin). Other excipients may be added to improve the formulation, and suppositories will be shaped in a form that facilitates administration. In other embodiments, liquid suppositories consisting of compstatin analogs dissolved or suspended in a liquid carrier suitable for rectal delivery to be applied with a small syringe may be used.

For the treatment of chronic or acute lung conditions in which complement activation is implicated, a preferred route of administration of a pharmaceutical composition is pulmonary administration. Accordingly, a pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, including replacement pulmonary surfactant, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intraarticular, intravitreal, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution can be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, in microbubbles for ultrasound-released delivery or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents including replacement pulmonary surfactants; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa.

Methods:

Another aspect of the invention features methods of regulating complement activation. In general, the methods comprise contacting a medium in which regulation of complement activation is desired with a compstatin analog of the present invention, wherein the contacting results in regulation of complement activation in the medium. The medium can be any medium in which regulation of complement activation is desired. In certain embodiments, the medium includes cells or tissues of an organism, including (1) cultured cells or tissues, (2) cells or tissues within the body of a subject or patient, and (3) cells or tissues that have been removed from the body of one subject and will be replaced into the body of the same patient (e.g., extracorporeal shunting of blood or autologous transplantation) or transferred to another patient. In connection with the latter embodiment, the medium may further comprise a biomaterial, such as tubing, filters or membranes that contact the cells or tissues during extracorporeal shunting. Alternatively, the medium may comprise biomaterials that are implanted into a subject.

In certain embodiments, the methods of regulating complement activation apply to living patients or subjects and comprise part or all of a method of treating the patient for a pathological condition associated with complement activation, particularly AP-mediated complement activation. Many such pathological conditions are known in the art (see, e.g., Holers, 2008, supra) and include, but are not limited to, as a typical hemolytic uremic syndrome (aHUS), dense deposit disease, age-related macular degeneration (AMD), paroxysomal nocturnal hemoglobinuria (PNH), cold agglutinin disease (CAD) rheumatoid arthritis (RA), systemic lupus erythematosus (SLE), several autoimmune and autoinflammatory kidney diseases, autoimmune myocarditis, multiple sclerosis, traumatic brain and spinal cord injury, intestinal and renal ischemia-reperfusion (IR) injury, spontaneous and recurrent pregnancy loss, anti-phospholipid syndrome (APS), Alzheimer's disease, asthma, anti-nuclear cytoplasmic antigen-associated pauci-immune vasculitis (Wegener's syndrome), non-lupus autoimmune skin diseases such as pemphigus, bullous pemphigoid, and epidermolysis bullosa, post-traumatic shock, certain forms of cancer, and atherosclerosis. In particular embodiments, the pathological condition has been associated with mutations and polymorphisms in the gene encoding FH and/or CD46, including but not limited to: AMD, aHUS and membranoproliferative glomerulonephritis type II (MPGN-II, also referred to as dense deposit disease (DDD)). In other embodiments, the compstatin analogs of the present invention are suitable for use as a substitute for Eculizumab or TT30 in treatment of diseases for which those agents are currently prescribed, or for which they are being developed in preclinical and clinical studies. Those diseases include, but are not limited to, aHUS, PNH, CAD and AMD.

The treatment methods typically comprise (1) identifying a subject with a disease or condition treatable by regulation of complement activation as described hereinabove, and (2) administering to the subject an effective amount of a compstatin analog of the invention using a treatment regimen and duration appropriate for the condition being treated. Development of appropriate dosages and treatment regimens will vary depending upon any number of factors, including but not limited to, the type of patient and type of disease state being treated, the age of the patient and the route of administration. The skilled artisan is familiar with the design of dosage regimens that take such variables into account. For instance, it will be apparent to the skilled artisan that oral administration of a compstatin analog of the invention will require a higher initial dosage, due to the lesser bioavailability from that route as compared with, e.g., intravenous injection.

Another aspect of the invention features a method of improving the C3 binding affinity of compstatin or a compstatin analog, utilizing the inventors' identification of a novel secondary binding site for compstatin on C3, as described herein. The method comprises adding an N-terminal component to the compstatin or compstatin analog that improves the binding affinity of the compstatin or compstatin analog to C3, C3b or C3c and, optionally, that improves the plasma stability and/or plasma residence time of the compstatin or compstatin analogy, as compared with an unmodified compstatin or compstatin analog under equivalent conditions.

Another aspect of the invention features a screening method that takes advantage of the inventors' identification of another potential compstatin binding site on C3 to produce compstatin analogs having improved C3 binding affinity. Candidate compstatin analogs comprising N-terminal components designed to access the binding site are constructed and analyzed, e.g., for compstatin binding affinity and/or complement inhibiting activity. In certain embodiments, the candidate compstatin analog is also designed to have increased plasma residence time, for instance, by binding albumin.

The following examples are provided to describe the invention in greater detail. They are intended to illustrate, not to limit, the invention.

EXAMPLE 1

This example describes the synthesis of compstatin analogs with N-terminal additions to albumin-binding small molecules.

Materials and Methods:

1. Synthesis of Albumin Affinity Tag

1.1 General Information

Tetrahydrofuran (THF), dichloromethane, and acetonitrile were purchased at ACS-grade from Fisher Scientific and dried via a solvent dispensing system prior to use in reactions. Other chemical reagents and ACS-grade solvents were purchased from Sigma Aldrich or Fisher Scientific and used without further purification. Unless otherwise stated, all reactions were performed under an atmosphere of $N_2$. All reactions and chromatography fractions were monitored by thin layer chromatography (TLC) on silica-gel-coated glass plates with a F254 fluorescent indicator. Visualization was achieved by UV absorption by fluorescence quenching or permanganate stain (1.5 g KMnO4, 10 g K2CO3, 1.25 mL 10% NaOH in 200 mL of H2O). Flash chromatography was performed using Silicycle SiliaFlash P60, 230-400 mesh silica gel. NMR spectra were recorded on a Varian Unity 400 or Unity Inova 500 spectrometer. Electrospray ionization time-of-flight mass spectrometry (ESI-TOF MS) was performed on a Waters Quattro II quadrupole spectrometer.

Reagents and conditions:
a KOH, EtOH, 0° C., 70%;
b 1) $H_2$, Pd/C, THF; 2) NaBH4, NaOH, $H_2O$, THF, 96% (two steps);
c DIPEA, $CH_2Cl_2$, 78%;
d 4,4-diphenylcyclo-hexanol, 1H-tetrazole, $^tBuOOH$, MeCN;
e 1) $NH_3$, MeOH; 2) LiOH, $H_2O$, THF, 50% (three steps).

1.2 Synthesis of 4,4-diphenyl-2-cyclohexen-1-one

Diphenylacetaldehyde (3.58 mL, 20.0 mmol) and 3-buten-2-one (2.46 mL, 30.0 mmol) were dissolved in anhydrous ethanol (15 mL) and chilled to 0° C. in an ice bath. Potassium hydroxide pellets (0.56 g, 10.0 mmol) were dissolved in anhydrous ethanol (10 mL) in a separate flask and chilled to 0° C. The cold KOH solution was added slowly to the aldehyde solution over 10 min, and the reaction was stirred at 0° C. for 3 h, over which time a precipitate formed. The reaction was concentrated under reduced pressure, and the resulting residue was partitioned between $H_2O$ and $Et_2O$. The mixture was acidified to pH 3 with 2 M aqueous HCl, and the layers were separated. The organic fraction was dried over $Na_2SO_4$, filtered and concentrated under reduced pressure. The crude material was purified by flash chromatography ($SiO_2$, 9:1 hexanes/EtOAc) to yield the product (3.47 g, 14.0 mmol, 70%) as a white solid. $R_f$ 0.52 (4:1 hexane/EtOAc). Spectral data matched those reported previously (Frimer et al., 1989, *J. Org. Chem.* 54, 4853).

1.3 Synthesis of 4,4-diphenylcyclohexanol

To a solution of 4,4-diphenyl-2-cyclohexen-1-one (3.40 g, 13.7 mmol) in THF (30 mL) was added 10% palladium on carbon (140 mg). The reaction vessel was flushed with hydrogen gas, and the system was sealed under a hydrogen atmosphere (1 atm) and stirred vigorously for 20 h. The catalyst was removed by filtration through Celite, washing with THF (15 mL), and the filtrate was chilled to 0° C. in an ice bath. Sodium borohydride (0.26 g, 6.85 mmol) was dissolved in 0.1 M aqueous NaOH (7 mL) in a separate flask and chilled to 0° C., then added dropwise to the organic solution. The system was warmed to room temperature and stirred for 2 h. The reaction was then chilled to 0° C., quenched with 2 M aqueous HCl (12 mL) and diluted with cold $H_2O$ (100 mL). The system was stirred at 0° C. for 30 min, over which time a white precipitate formed. The precipitate was isolated by filtration, washed with cold $H_2O$ and dried under reduced pressure to yield the product (3.32 g, 13.2 mmol, 96% over two steps) as a white solid. $R_f$ 0.26 (4:1 hexanes/EtOAc). Spectral data matched those reported previously (Amedio Jr. et al., 1998, *Synth. Comm.* 28, 3895).

1.4 Synthesis of ethyl 6-[(2-cyanoethyl)(N,N-diisopropylamino)phosphino]oxyhexanoate Ethyl 6-hydroxyhexanoate (2.44 mL, 15.0 mmol) and diisopropylethylamine (10.4 mL, 60.0 mmol) were dissolved in $CH_2Cl_2$ (60 mL). 2-Cyanoethyl-N,N-diisopropylchlorophosphoramidite (3.51 mL, 15.8 mmol) was added dropwise, and the reaction was stirred for 2 h. The reaction was washed with ice-cold saturated aqueous NaHCO$_3$, dried over Na$_2$SO$_4$, filtered and concentrated under reduced pressure. The crude material was purified by flash chromatography (SiO$_2$, 9:1 hexane/EtOAc with 0.1% Et$_3$N) to yield the product (4.20 g, 11.7 mmol, 78%) as a colorless liquid. R$_f$ 0.80 (2:1 hexane/EtOAc). Spectral data matched those reported previously (Raddatz et al., 2002, *Nucleic Acids Res.* 30, 4793).

1.5 Synthesis of ABM2

Synthesis was performed with modification from a previous report (Zobel et al., 2003, *Bioorg. Med. Chem. Lett.* 13, 1513). Ethyl 6-[(2-cyanoethyl)(N,N-diisopropylamino) phosphino]oxyhexanoate (2.90 g, 8.05 mmol) and 4,4-diphenylcyclohexanol (2.13 g, 8.45 mmol) were combined in acetonitrile (30 mL). A 0.45 M solution of 1H-tetrazole in acetonitrile (18.8 mL, 8.45 mmol) was added, and the reaction was stirred under N$_2$ for 3 h. A 70% w/w aqueous solution of tert-butylhydroperoxide (8 mL) was added, and the reaction stirred for an additional 1 h, then concentrated under reduced pressure. The resulting residue was taken up in EtOAc, washed with 10% Na$_2$S$_2$O$_3$, saturated aqueous NaHCO$_3$ and brine, dried over Na$_2$SO$_4$, filtered and concentrated under reduced pressure. The crude material was purified by flash chromatography (SiO$_2$, 1:1 hexanes/EtOAc with 0.1% Et$_3$N) to yield a colorless oil (R$_f$ 0.13, 1:1 hexanes/EtOAc). This oil was taken up in 2 M ammonia in methanol (80 mL) and stirred under N$_2$ for 12 h to remove the cyanoethyl substituent. The reaction was concentrated, and the resulting oil was taken up in THF (10 mL) and chilled to 0° C. in an ice bath. A 2 M aqueous solution of lithium hydroxide (5 mL) was added, and the reaction was warmed to room temperature and stirred for 2 h to hydrolyze the ethyl ester. The reaction was concentrated and taken up in water (100 mL). The solution was acidified to pH 2 with 2 M aqueous HCl, forming a white precipitate that was extracted with EtOAc (3×50 mL). The organic fractions were combined, dried over Na$_2$SO$_4$, filtered and concentrated to yield the product (1.94 g, 4.35 mmol, 54% over three steps) as an off-white solid after lyophilization from 1:1 benzene/acetonitrile. R$_f$ 0.45 (4:1:1 BuOH/H$_2$O/AcOH). $^1$H NMR (CD$_3$OD, 500 MHz) δ 7.32-7.20 (m, 8H), 7.10 (q, J=7.5 Hz, 2H), 4.33 (m, 1H), 3.89 (q, J=6.5 Hz, 2H), 2.60 (m, 2H), 2.28 (t, J=7.5 Hz, 2H), 2.19 (m, 2H), 1.89 (m, 2H), 1.74 (m, 2H), 1.66-1.58 (m, 4H), 1.45-1.39 (m, 2H). $^{13}$C NMR (CD$_3$OD, 125 MHz) δ 177.5, 149.2, 148.6, 129.3, 129.1, 128.2, 127.9, 126.6, 75.2, 66.8, 46.6, 34.9, 34.0, 31.3, 30.8, 26.4, 25.7. $^{31}$P NMR (CD$_3$OD, 200 MHz) δ 0.64. MS (ESI): calc. for C$_{24}$H$_{32}$O$_6$P 447.1937, found 447.1934.

2. Peptide Synthesis and Purification

2.1 Reagents.

Rink amide MBHA resin (100-200 mesh, substitution: 0.36 mmole/g), Oxyma (ethyl 2-cyano-2-[hydroxyimino] acetate) and the following Fmoc-amino acids were obtained from Novabiochem (San Diego, Calif.): Ile, Cys(Trt), Val, D-Tyr(tBu), Gln(Trt), Asp(OtBu), Trp(Boc), Sar, Ala, His (Trt), Arg(Pbf), MeIle. DIC, Fmoc-Trp(Me)-OH, Fmoc-Lys (biotin)-OH and Fmoc-AEEEA (miniPEG=AEEEA) were purchased from AnaSpec (San Jose, Calif.). DMF, NMP and DCM were obtained from Fisher Scientific (Pittsburgh, Pa.). All other chemical reagents for synthesis were purchased from Sigma-Aldrich (St. Louis, Mo.) and used without further purification. ABMT was obtained from Enamine (Monmouth Jct., N.J.; EN300-09570; 3-(naphthalene-2-sulfonamido)propanoic acid). ABM2 was synthesized according to established protocols as described above.

2.2 Procedures.

Synthesis of compstatin analogs was performed using solid-phase peptide synthesis as previously described. (Qu et al., 2011, *Mol. Immunol.* 48, 481; Qu et al., 2013, *Immunobiology* 218, 496). Rink amide MBHA resin was used for the synthesis of all peptides, unless otherwise specified. After deprotection of the Fmoc group (5% piperazine in NMP with 0.1 M Oxyma), the resin was washed with NMP and DCM, and then individual amino acids were coupled to the resin. For each coupling, 3 equivalents of the amino acid, Oxyma, and DIC were used, with 10 min pre-activation in NMP. All couplings were performed for 1 h and monitored by either Kaiser test or chloranil test. In case of a positive test result, the coupling was repeated until a negative test result was observed. In the cases of the conjugation of albumin-binding molecules, the appropriate acid was coupled to the amino terminus of the peptide on resin (ABM1: DIPEA, HATU, DMF; ABM2: DIPEA, PyBOP, NMP, DCM) (Zobel et al., 2003, supra; Koehler et al., 2002, *Bioorg. Med. Chem. Lett.* 12, 2883). In the cases of the biotin-labeled peptides, Fmoc-Lys(biotin)-OH was used as the first amino acid to be coupled on the resin, followed by miniPEG and compstatin sequence. Upon completion of the solid phase synthesis, the peptides were cleaved from the resin with a mixture of 90% TFA, 5% thioanisole, 3% EDT and 2% anisole for 2 h. The peptides were precipitated and washed three times with ice-cold diethyl ether. The liquid was separated by centrifugation and decanted. The crude peptides were dissolved in acetonitrile:water (1:1) and filtered through a Puradisc syringe filter (0.45 μm PVDF, Whatman). The pH of the solution was adjusted to 7-8 using 5% aqueous ammonium hydroxide. Dilute hydrogen peroxide (1:100, 2 eq.) was added to the solution under vigorous stirring. Once the reaction was completed (as detected by MALDI mass spectrometry), TFA was added to lower the pH to 2, and the solution was lyophilized. The crude peptide was then purified by reverse phase HPLC (XBridge Prep C18, 5 μm, 30×150 mm column) and eluted with a gradient of acetonitrile in aqueous 0.1% TFA solution at a flow rate of 10 mL/min. The purified peptides were >95% pure as determined by analytical HPLC (XBridge C18, 5 μm, 4.6×150 mm column). The mass of each peptide was confirmed using MALDI micro MX instrument (Waters, Milford, Mass.) or a SYNAPT G2-S high-resolution mass spectrometer (Waters).

Results:

Previous analysis of the co-crystal structure of a compstatin analog with the target protein fragment C3c revealed that both termini of the cyclic peptide are minimally engaged in binding site contacts and may be amenable for modification.[22] For initial studies, the previously described albumin-binding tags (ABM1 and ABM2 with a carboxylic acid group) were coupled to the N-terminus of compstatin analog Cp20 through an amide linkage (FIG. 5).[8,17,18] Following cleavage from the resin, each peptide was oxidized with hydrogen peroxide to form the intramolecular disulfide bond. All peptides were purified by reversed-phase high-performance liquid chromatography (RP-HPLC), resulting in average overall yields of 9-16% after lyophilization.

EXAMPLE 2

Compstatin analogs synthesized by the methods described in Example 1 were measured for C3 binding and complement-inhibitory activity, plasma protein binding and plasma stability.

Materials and Methods:
1. SPR Analysis
1.1 Interaction of Compstatin Analogues with C3b.

The binding affinity and kinetic profiles of the compstatin analogs with C3b was characterized by surface plasmon resonance (SPR) using a Biacore 3000 instrument (GE Healthcare, Corp., Piscataway, N.J.) using previously established assay conditions.[7] Data were recorded at 25° C. using PBS-T (10 mM sodium phosphate, 150 mM NaCl, 0.005% Tween-20, pH 7.4) as running buffer. Biotinylated C3b was captured on flow cells of a streptavidin sensor chip (GE Healthcare) at densities of about 3000 and 5000 resonance units (RU); untreated flow cells were used as a reference surface. A single cycle approach was used for kinetic analysis; sets of five increasing concentrations of each compound (2.5-40 nM) were injected over the chip surface consecutively in a single cycle without regeneration at a flow rate of 30 μL/min. Individual injections within a cycle were 2 min long with a 5-min dissociation between injections. After the end of the last injection, a 40-min dissociation time was allowed. The corresponding untagged compstatin analog (C20 or Cp40) was included in each experimental series as an internal control. Data were processed in Scrubber (v2.0c; Bio-Logic Software, Campbell, Australia); the signals from an untreated flow cell and an ensemble of buffer blank injections were subtracted to correct for buffer effects and injection artifacts. The kinetic evaluation was performed in BiaEvaluation using a single cycle kinetic template (kindly provided by GE Healthcare) by globally fitting each data set to a 1:1 Langmuir binding model to achieve association and dissociation rates ($k_a$ and $k_d$, respectively); the equilibrium dissociation constant ($K_D$) was calculated from the equation $K_D=k_d/k_a$ (FIG. 1). Each assay was performed at least twice.

1.2 Interaction of ABM-Compstatin Conjugates with Albumin.

Figure 2:
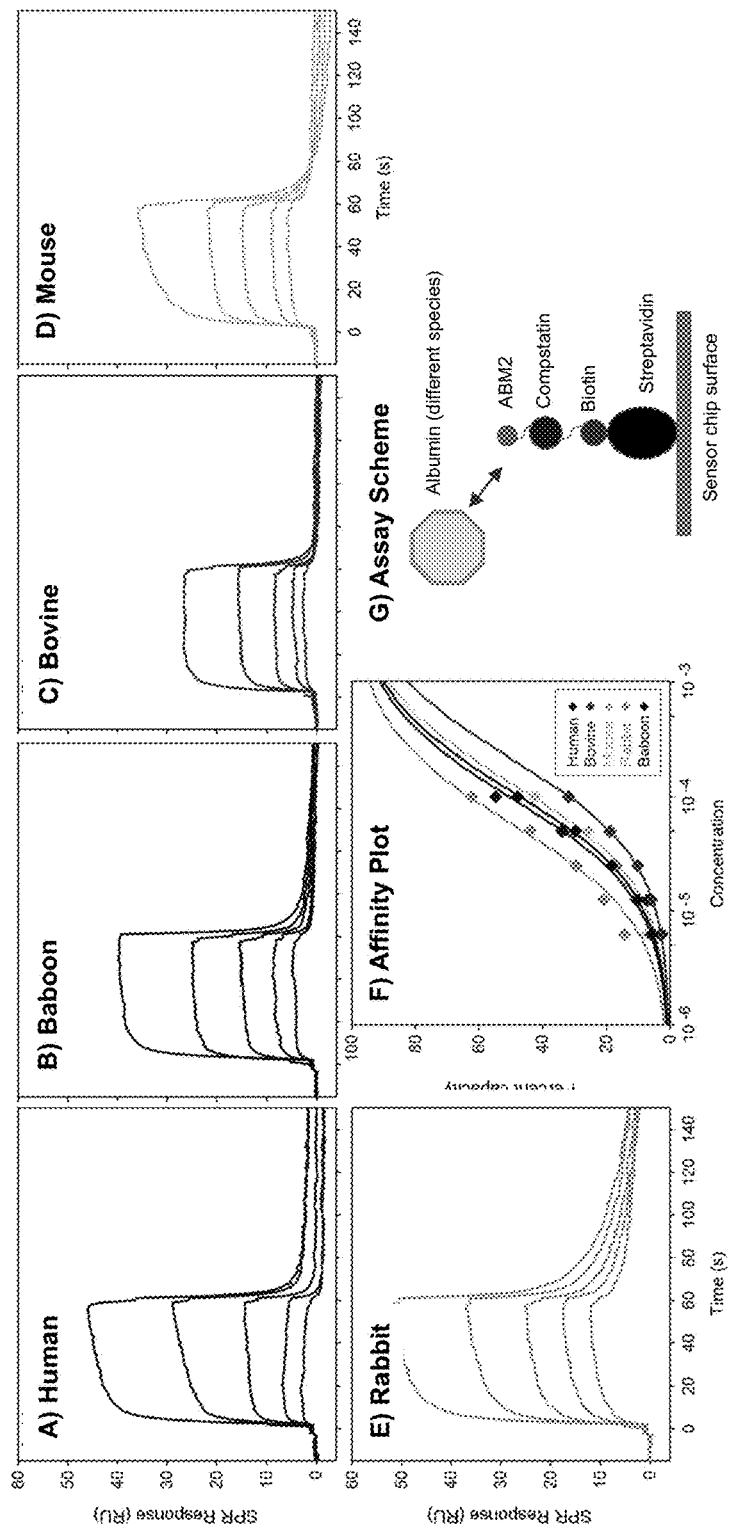
FIG. 2. Evaluation of interaction profiles between immobilized ABM2-Cp20 with albumin from different species. A-E) Albumin binding responses as measured by SPR. F) Affinity estimation by fitting concentration plots to a single-binding-site model (rabbit, top line; human, second line from top; baboon, third line from top; mouse, fourth line from top; bovine, bottom line). G) Schematic representation of the albumin-binding assay.

ABM2-Cp20-miniPEG-Lys(biotin) and Cp40-miniPEG-Lys(biotin) were synthesized via SPPS as described above. Streptavidin was immobilized on all flow cells of CM5 sensor chips (GE Healthcare) using standard amine coupling under 30° C. Biotinylated ABM2-Cp20 and Cp40 were captured on individual flow cells at densities of about 100 resonance units (RU); untreated flow cells were used as a reference surface. Sets of five increasing concentrations (6.3-100 μM) of albumin from different species (human, mouse, bovine, rabbit and baboon) were injected over the chip surface (FIG. 2). Data were recorded at 25° C. using PBS-T (10 mM sodium phosphate, 150 mM NaCl, 0.005% Tween-20, pH 7.4) as running buffer. Data were processed in Scrubber (v2.0c; Bio-Logic Software, Campbell, Australia); the signals from an untreated flow cell and buffer blank injections were subtracted. Apparent binding affinities ($K_D$ app) were calculated by fitting the steady state responses to a single-binding-site model.

1.3 Competition Analysis of ABM2-Cp20.

Figure 3:
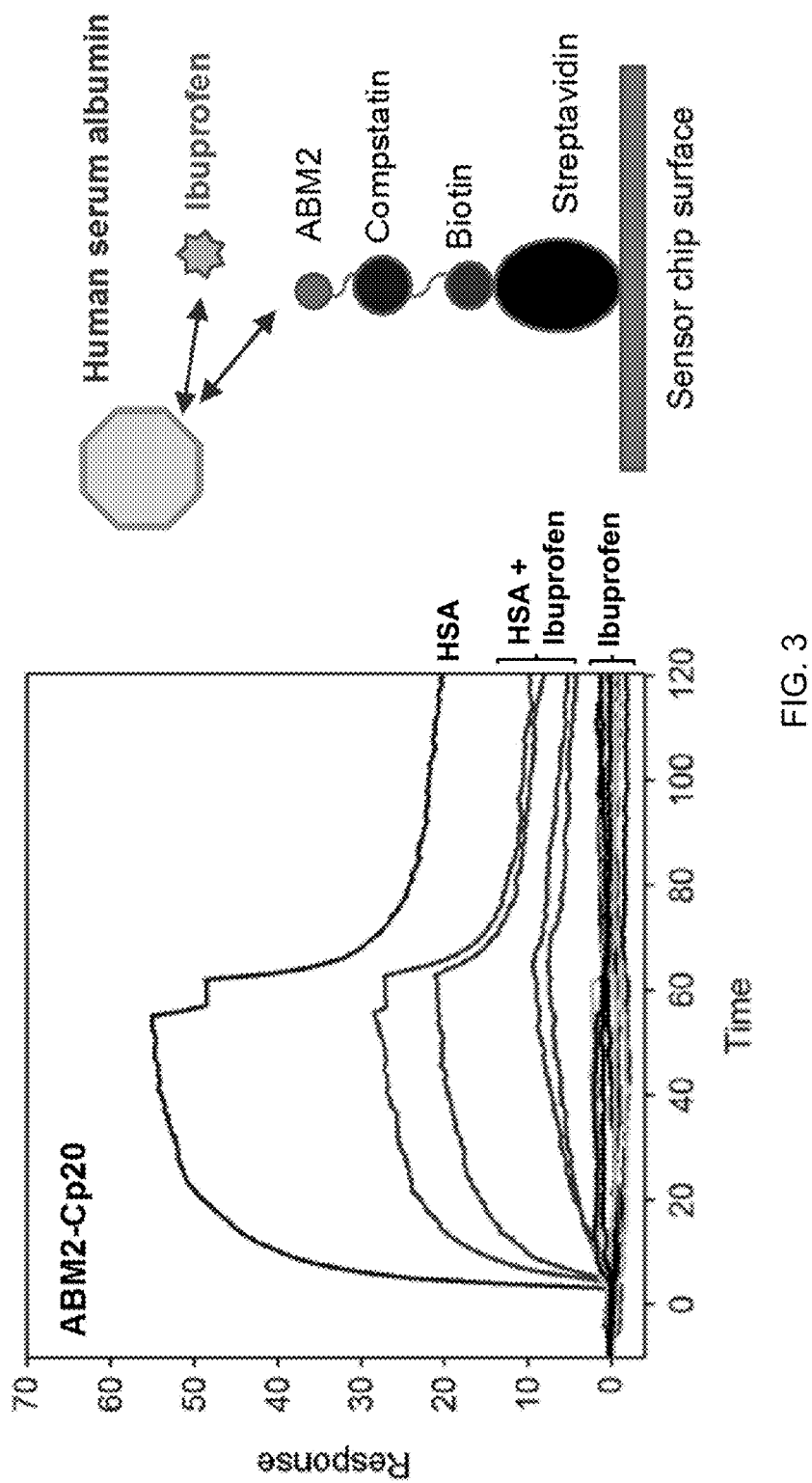
FIG. 3. Competition between immobilized ABM2-Cp20 and soluble ibuprofen for binding to human serum albumin (HSA). Ibuprofen (flat lines along the X-axis) does not bind to ABM2-Cp20. Increasing concentrations of ibuprofen in solution (50-500 µM; four lines between 0 and 25) suppress the binding signal of HSA (top line). The right panel shows a scheme of the competitive assay setup.

Human serum albumin (50 μM), (S)-ibuprofen (50, 100, 250, 500 μM), and mixtures of HSA and ibuprofen were individually injected to the ABM2-Cp20-miniPEG-Lys(biotin) immobilized sensor chip (as described above). Data were recorded at 25° C. using PBS-T (10 mM sodium phosphate, 150 mM NaCl, 0.005% Tween-20, pH 7.4) as running buffer, and untreated flow cells were used as a reference surface. (S)-ibuprofen shows the dose-dependent blockade of HSA binding to the sensor chip (FIG. 3).

2. Inhibition of Complement Activation

Figure 4:
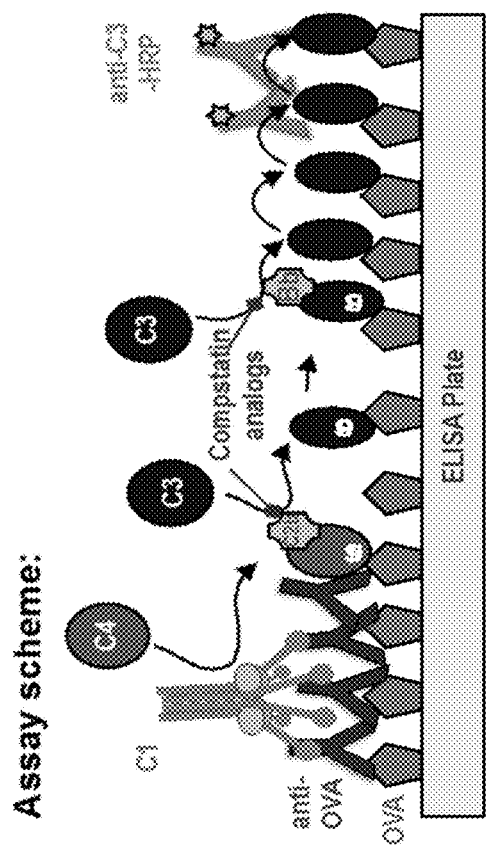
FIG. 4. Representative examples of complement inhibition by ABM-conjugates and parent peptides as measured by ELISA. A scheme of the assay is shown on the right.
Figure 4:
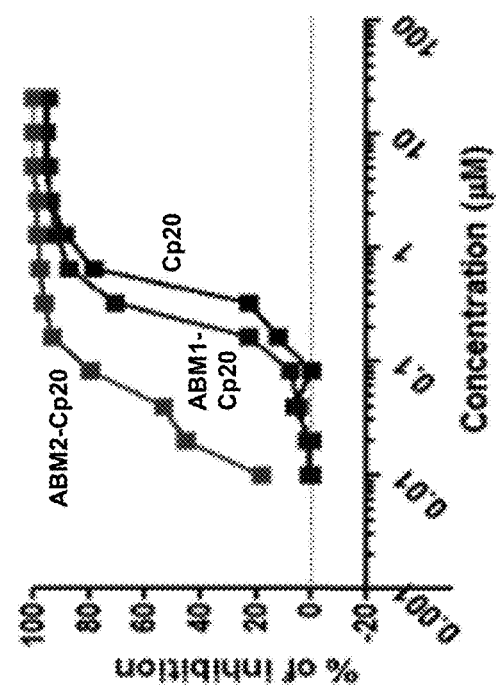

The potency of the compstatin analogs to inhibit complement activation initiated via the classical pathway was assessed by an established ELISA (Katragadda et al., 2006, J. Med. Chem. 49, 4616). Each peptide was dissolved in water, and its concentration was determined by Nanodrop using the absorbance at 280 nm. Inhibition of immune complex-mediated complement activation by each peptide was determined over a concentration range of 0.01 μM and ~10 μM as described before (Katragadda et al., 2006, supra). The percent inhibition was plotted against the peptide concentration, and the resulting data set was fitted to the logistic dose-response function to obtain $IC_{50}$ values (FIG. 4).

3. Plasma Protein Binding (Equilibrium Dialysis)
3.1 Reagents and Materials.

A rapid equilibrium dialysis (RED) device with inserts (MWCO 8 K) was used (Thermo Scientific). C3-depleted serum (product no. A314) was purchased from Complement Technology, Tyler, Tex. Purified C3 (Complement Technology, A113c) was added to C3-depleted serum at a defined, physiologically relevant concentration (5 μM) to maintain the sample matrix and inhibitor-target ratio in comparative experiments (referred to as C3-positive serum).

3.2 Procedure for Equilibrium Dialysis.

Equilibrium dialysis using RED device was performed to determine the plasma protein binding. The inserts were soaked in water for 10 min before discarding the water (twice), and then used immediately (Waters et al., 2008, J. Pharm. Sci. 97, 4586). A mixture of 90 μL C3-depleted or C3-positive serum and 10 μL compstatin sample (5 or 10 μM) in PBS buffer (10% DMSO, 0.5% Tween 20, 0.2% sodium azide) was placed in the plasma chamber, and 300 μL PBS buffer (1% DMSO and 0.05% Tween 20) was placed in the buffer chamber. The final DMSO concentration of the dialysis system was 1%. The plate was covered with a sealing tape and incubated at 37° C. on an orbital shaker (200 rpm) for 24 h. Each sample was analyzed at least twice.

3.3 Procedure for Sample Analysis.

A 50-μL aliquot of each post-dialysis sample from both the plasma and buffer chambers was pipetted into separate LoBind tubes (Eppendorf). The samples from plasma chambers were diluted with 50 μL PBS, while samples from buffer chambers were diluted with C3-depleted, or C3 positive serum (matrix match). All samples were diluted to 100 μL using 4% $H_3PO_4$ to dissociate the peptides. The mixture was then subjected to solid phase extraction (Oasis® HLB 96-well Plate, 10 mg Sorbent per Well, 30 μm Particle Size) and eluted with 200 μL 65% ACN/0.1% formic acid (Cp20) or eluted with 200 μL 85% ACN/0.1% formic acid (ABM2-Cp20). The eluent was injected into the UPLC-HDMS system consisting of an online ACQUITY UPLC (Waters BEH C18 column, 130 Å, 1.7 μm, 2.1 mm×150 mm) coupled to a SYNAPT G2-S HDMS instrument equipped with an ESI source (capillary voltage was set to 3.2 kV, the cone voltage to 30 V and the source temperature to 120° C.). MS peak areas of the peptide were determined by integration for the quantification (Qu et al., 2013, supra). The unbound fraction of the peptide in plasma (% free) was calculated from the ratio of the buffer side response to the plasma side response. The bound fraction of the compound was calculated as follows: % bound=100−% free.

4. Binding Model of ABM2-Cp20

Moloc (Gerber Molecular Design, URL is moloc.ch) was used for the docking study that evaluated the binding of ABM2-Cp20 to the compstatin binding site based on the available co-crystal structure of C3c with compstatin analog 4W9A (PDB code: 2QKI) (Janssen et al., 2007, J. Biol. Chem. 282, 29241). The initial structural model of the ABM2-Cp20 was manually built based on the C3c-bound structure of 4W9A and docked into the compstatin binding pocket of human C3c. The modeling image was rendered using PyMol (URL is pymol.org).

Figure 5:
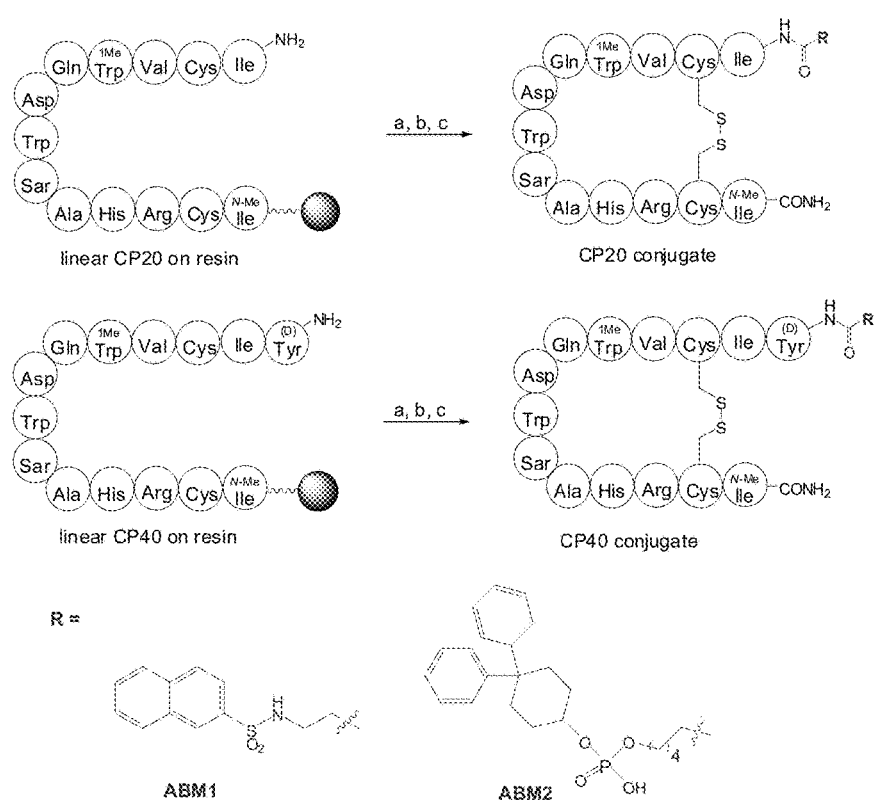
FIG. 5. Schematic diagram of synthesis of conjugates between compstatin analogs Cp20 (Ac-Ile-[Cys-Val-Trp(Me)-Gln-Asp-Trp-Sar-Ala-His-Arg-Cys]-mIle-NH$_2$; SEQ ID NO:2) and Cp40 ((D)Tyr-Ile-[Cys-Val-Trp(Me)-Gln-Asp-Trp-Sar-Ala-His-Arg-Cys]-mIle-NH$_2$; SEQ ID NO:3) with albumin-binding molecules (shown to the right of the reaction arrows; R=ABM1 or ABM2). Steps a, b, and c of the synthesis reaction are indicated above the reaction arrow. Reagents and conditions: (step a) coupling of RCOOH: DIPEA, HATU, DMF (R=ABM1); or DIPEA, PyBOP, NMP, DCM (R=ABM2);[17,18] (step b) resin cleavage with 90% TFA, 5% thioanisole, 3% EDT and 2% anisole; (step c) cyclization with hydrogen peroxide, as in Example 1.
Figure 6A:
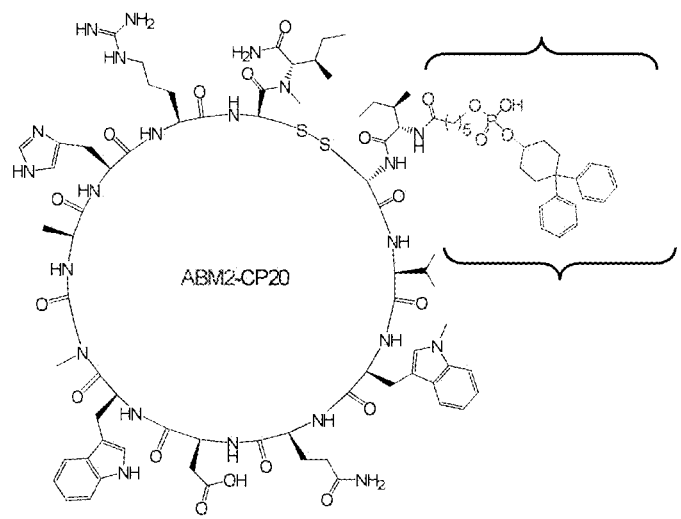
(FIG. 6a) Structure of ABM2-Cp20 with the ABM2 tag (indicated by brackets). Cp20 is represented by SEQ ID NO:2.
Figure 6B:
(FIG. 6b) Docking of ABM2-Cp20 (space filling model) into the compstatin binding site of C3c (PDB code: 2QKI), shown as a ribbon diagram.
Figure 6C:
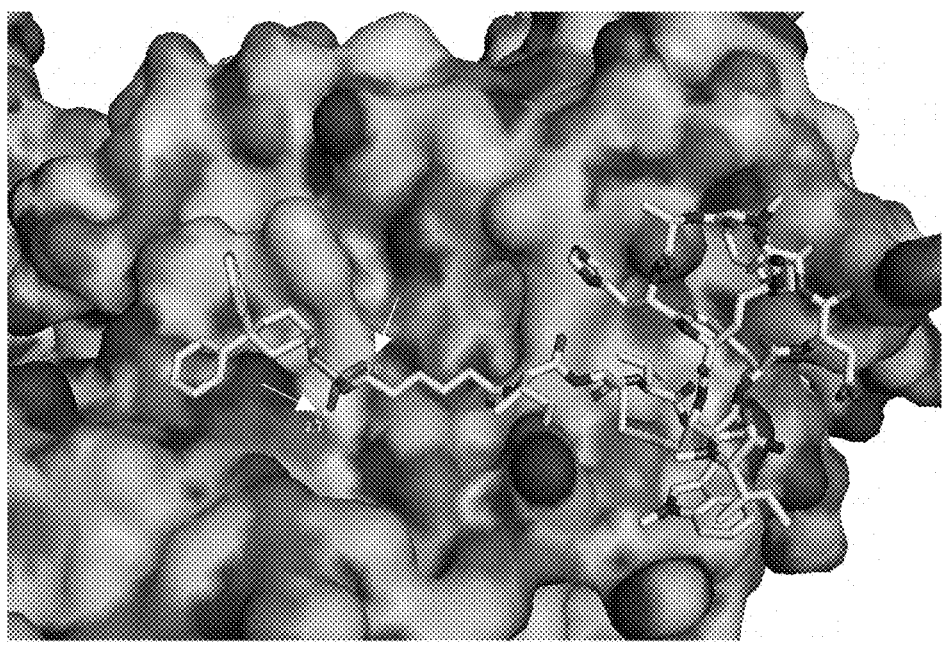
(FIG. 6c) ABM2-Cp20 is shown as stick on the surface of C3c (SEQ ID NO:5). The hydrogen bonding between ABM2-Cp20 and K386 of C3c predicted from the computational analysis is shown in dashed lines. The phosphate ester group of ABM2 forms two hydrogen bonds with the terminal amino group and backbone amide of Lys386 in C3c. Arrows point to the dashed lines showing these two interactions.

Results:

To confirm maintenance of target binding affinity after addition of the albumin-binding tags, the synthesized compstatin conjugates were assayed using surface plasmon resonance (SPR) by injecting them over site-specifically immobilized C3b.[7,23] Due to the slow dissociation rate of these compounds, single-cycle kinetics approach was used to improve the assay efficiency.[24] The SPR responses of all peptides were fitted to a 1:1 Langmuir binding model to obtain kinetic association and dissociation rate constants ($k_a$, $k_d$) and binding affinities ($K_D$; Table 1). As expected, conjugation of ABMT to the N-terminus of Cp20 fully maintained the target binding affinity; the slight improvement compared to the parent peptide may be explained by additional hydrophobic contacts of the new N-terminus with the binding site of C3 as it had been observed with Cp40.[7] Surprisingly, however, the conjugation with ABM2 led to a 20-fold improvement in binding affinity ($K_D$=150 pM), rendering ABM2-Cp20 the most potent compstatin analog described so far. To further explore the potential of ABM2-mediated enhancement of compstatin affinity, we conjugated ABM2 to the N-terminus of Cp40 (FIG. 5). In contrast to Cp20, the addition of ABM2 to Cp40 led to a comparatively minor improvement of affinity (Table 1). Analysis of the compstatin binding site using a structural model of ABM2-Cp20 suggested that the alkyl linker in ABM2 may ideally align the diphenyl-cyclohexanol moiety with a shallow groove formed by macroglobulin domain 4 of C3c β-chain (FIG. 6). In the case of ABM2-Cp40, the presence of an additional amino acid at the C-terminus would lead to a less preferred placement of this moiety.

TABLE 1

Evaluation of C3b interaction profiles of compstatin conjugates[a]

| Peptide | $k_a$ ($10^6$ M$^{-1}$s$^{-1}$) | $k_d$ ($10^{-3\ s-1}$) | $K_D$ (nM) |
|---|---|---|---|
| Cp20 | 2.3 ± 0.7 | 6.7 ± 2.9 | 2.9 ± 0.4 |
| ABM1-Cp20 | 1.7 ± 0.1 | 3.5 ± 0.1 | 2.0 ± 0.1 |
| ABM2-Cp20 | 2.7 ± 0.9 | 0.4 ± 0.1 | 0.15 ± 0.06 |
| Cp40 | 2.8 ± 0.6 | 1.3 ± 0.2 | 0.48 ± 0.09 |
| ABM2-Cp40 | 1.8 ± 0.2 | 0.5 ± 0.2 | 0.26 ± 0.09 |

[a]Single-cycle kinetic analysis of compstatin conjugates was performed. Sets of five increasing concentrations were consecutively injected over a C3b surface (3000-5000 RU density) in a single cycle. The processed signals were fitted to a 1:1 binding model.

As the binding of ABM-compstatin conjugates to albumin in circulation may affect their complement-directed potency, we also evaluated the inhibitory activity of all peptides toward immune complex-induced complement activation in human plasma using an established ELISA format.[25] Compared with the parent peptides, the conjugates retain or improve the inhibitory activity (Table 2; FIG. 4), thereby indicating that they are able to bind their target despite the high plasma concentration of albumin.

TABLE 2

Complement inhibition potency of compstatin conjugates[a]

| Peptide | IC$_{50}$ (μM) |
|---|---|
| Cp20 | 0.26 ± 0.12 |
| ABM1-Cp20 | 0.2 ± 0.00 |
| ABM2-Cp20 | 0.17 ± 0.11 |

TABLE 2-continued

Complement inhibition potency of compstatin conjugates[a]

| Peptide | IC$_{50}$ (μM) |
|---|---|
| Cp40 | 0.14 ± 0.05 |
| ABM2-Cp40 | 0.08 ± 0.03 |

[a]Complement inhibition assay based on initiation via the classical pathway.

To confirm the albumin-directed activity of the ABM-compstatin conjugates and further explore their simultaneous binding to C3 and albumin, we performed additional SPR binding studies. For this purpose, a ABM2-Cp20 derivative with C-terminal biotinylation was synthesized as a probe compound. In addition, biotinylated Cp40 (without an ABM2 tag) was used as control. The biotinylated peptides were immobilized on a streptavidin-coated SPR sensor chip, and the interactions with albumins from different species (human, baboon, bovine, rabbit and mouse) were characterized (Table 3; FIG. 2). Notably, given the narrow species specificity of compstatin for C3 from human and NHP, only the binding to human and baboon albumin is of direct importance for use in disease models. Also, limitations in the available concentration range of albumin only allows for an estimation of affinity values. Nevertheless, the apparent binding affinity of ABM2-Cp20 with human serum albumin ($K_{D\ app}$=97 μM; Table 3) was similar to that of MS-325, which uses the same tag ($K_D$=164 μM).[26] The apparent affinities of albumin from other species to ABM2-Cp20 were in a similar range, with baboon albumin showing values nearly identical to those of the human form (Table 3). In contrast, none of the albumins bound significantly to the compstatin control lacking the ABM2 tag (data not shown). These results demonstrate that conjugation to ABMs enables compstatin analogs to bind serum albumins; importantly, ABM2-Cp20 binds more tightly to C3 than to albumin (with affinities of ~0.2 nM vs. ~100 μM), thereby indicating minimal interference with the pharmacodynamic profile of the peptide.[18]

TABLE 3

Evaluation of albumin interaction profiles to immobilized ABM2-Cp20[a]

| Albumin species | Apparent binding affinity |
|---|---|
| Human | 97 ± 2 μM |
| Bovine | 208 ± 5 μM |
| Mouse | 134 ± 3 μM |
| Rabbit | 64 ± 2 μM |
| Baboon | 106 ± 3 μM |

[a]The interactions of ABM2-Cp20 with albumins were characterized by multi-cycle analysis. Sets of five increasing concentrations of albumin from different species (6.3-100 μM) were injected over the chip surface. The processed signals were fit to a single binding site model.

To confirm the albumin binding mode of ABM2-Cp20, an SPR-based competition assay was used. Fluorescent probe displacement studies showed that MS-325 binds primarily to site II on HSA, since MS-325 can displace site II ligands rather than site I ligands (such as warfarin).[27] Ibuprofen, which binds to the site II of human serum albumin ($K_D$=0.37 μM), was chosen as a probe of site II ligands.[28,29] When HSA (50 μM) was injected to the ABM2-Cp20 sensor chip in the presence of ibuprofen (50-500 μM), a dose-dependent inhibition of albumin binding to the conjugate was observed (FIG. 3), which suggests that ABM2-Cp20 indeed binds primarily to site II in a similar manner to MS-325.

Previous pharmacokinetic studies of Cp20 in NHP revealed a distinctive target-driven elimination profile, in which the strong binding to the abundant plasma protein C3

(~1 mg/ml) defines the slow terminal elimination of the compound; unbound peptide in excess of the plasma C3 level is excreted more rapidly.[7] This strong influence of target binding on the elimination profile was further supported by the fact that the more potent Cp40 had a significantly lower half-life than Cp20 (12 vs. 9 h).[7] The ~20-fold increased binding affinity of ABM2-Cp20 for C3 itself is therefore expected to contribute to an enhanced pharmacokinetic profile. In addition, however, the binding to albumin is considered important as it would facilitate the maintenance of target-saturating inhibitor concentration. In order to assess the influence of and cooperation between C3 and albumin binding in the case of Cp20 and ABM2-Cp20, we performed in vitro plasma protein binding studies assay using rapid equilibrium dialysis (RED).[30] The free fractions of each peptide (% free) were determined by mass spectrometry from the concentration ratios between the buffer and plasma side after 24 h of incubation at 37° C., and used to calculate the protein-bound fraction (% bound). Two peptide concentrations (5 and 10 µM) were selected that represent inhibitor levels relevant for therapeutic complement inhibition.[7,9] When C3-depleted serum was used to assess plasma protein binding in absence of target-mediated effects, the conjugation of the ABM2 tag to Cp20 resulted in a profound increase of the bound fraction when compared to the parent peptide (Table 4). Reconstitution of the serum to a defined C3 concentration within the physiological range (5 µM) leveled the difference of the two peptides to >99% bound at an equimolar target-inhibitor ratio, thereby clearly reflecting the strong influence of target binding. When 10 µM peptide concentrations in excess of C3 were used, the influence of the ABM2 tag became again more pronounced (Table 4). These studies clearly indicate that, when compared to its parent peptide, ABM2-Cp20 is more likely to reside in plasma independently of C3 due to its binding to albumin. The observed profile is expected to reduce the comparatively rapid elimination of excessive peptide and facilitate the maintenance of target-saturating inhibitor levels. While the lower solubility of ABM2-Cp20 likely requires adjustment in the formulation for parenteral injection, it will be interesting to evaluate the pharmacokinetic profile in NHP in the future.

TABLE 4

Plasma protein binding profiles of compstatin conjugates[a]

| Peptide | C3-depleted serum % bound | C3-positive serum[b] % bound |
|---|---|---|
| Cp20 (5 µM) | 7 ± 3 | >99 |
| ABM2-Cp20 (5 µM) | >99 | >99 |
| Cp20 (10 µM) | 3 ± 1 | 84 ± 1 |
| ABM2-Cp20 (10 µM) | >99 | >99 |

[a]Peptides were extracted from post-dialysis samples using solid phase extraction (SPE) and analyzed by reversed phase ultra performance liquid chromatography coupled to high definition mass spectrometry (UPLC-HDMS) as described in the Supporting Information.
[b]A defined, physiological amount of purified C3 (5 µM) was added to C3-depleted serum.

Summary.

The examples above describe a new series of compstatin derivatives with significant improvements regarding both potency and pharmacokinetic properties via the introduction of an albumin affinity tag. Such enhanced complement inhibitors will be useful for the systemic treatment of chronic complement-mediated diseases, as they may allow for sustained maintenance of therapeutic inhibitor levels at reduced dose intervals. Additionally, the identification of a secondary/extended binding site for N-terminally tagged compstatin analogs should facilitate the rational design of complement inhibitors with enhanced pharmacokinetic and pharmacodynamic profiles.

REFERENCES

[1] D. Ricklin, J. D. Lambris, *J. Immunol.* 2013, 190, 3831-8.
[2] A. Sahu, B. K. Kay, J. D. Lambris, *J. Immunol.* 1996, 157, 884-891.
[3] D. Ricklin, J. D. Lambris, *Adv. Exp. Med. Biol.* 2008, 632, 273-92.
[4] I. Kourtzelis, M. M. Markiewski, M. Doumas, S. Rafail, K. Kambas, I. Mitroulis, S. Panagoutsos, P. Passadakis, V. Vargemezis, P. Magotti, et al., *Blood* 2010, 116, 631-639.
[5] R. Silasi-Mansat, H. Zhu, N. I. Popescu, G. Peer, G. Sfyroera, P. Magotti, L. Ivanciu, C. Lupu, T. E. Mollnes, F. B. Taylor, et al., *Blood* 2010, 116, 1002-1010.
[6] I. Kourtzelis, S. Rafail, R. A. DeAngelis, P. G. Foukas, D. Ricklin, J. D. Lambris, *FASEB J.* 2013, 27, 2768-76.
[7] H. Qu, D. Ricklin, H. Bai, H. Chen, E. S. Reis, M. Maciejewski, A. Tzekou, R. A. DeAngelis, R. R. G. Resuello, F. Lupu, et al., *Immunobiology* 2013, 218, 496-505.
[8] H. Qu, P. Magotti, D. Ricklin, E. L. Wu, I. Kourtzelis, Y.-Q. Wu, Y. N. Kaznessis, J. D. Lambris, *Mol. Immunol.* 2011, 48, 481-9.
[9] A. M. Risitano, D. Ricklin, Y. Huang, E. S. Reis, H. Chen, P. Ricci, Z. Lin, C. Pascariello, M. Raia, M. Sica, et al., *Blood* 2014, 123, 2094-2101.
[10] T. Maekawa, T. Abe, E. Hajishengallis, K. B. Hosur, R. A. DeAngelis, D. Ricklin, J. D. Lambris, G. Hajishengallis, *J. Immunol.* 2014, 192, 6020-6027.
[11] D. Ricklin, J. D. Lambris, *J. Immunol.* 2013, 190, 3839-47.
[12] L. Pollaro, C. Heinis, *Medchemcomm* 2010, 1, 319.
[13] F. Kratz, *J. Control. Release* 2008, 132, 171-183.
[14] Z. H. Gao, G. Bai, J. Q. Chen, Q. Zhang, P. W. Pan, F. Bai, P. Geng, *Biosci. Biotechnol. Biochem.* 2009, 73, 688-694.
[15] J. F. Langenheim, W. Y. Chen, *J. Endocrinol.* 2009, 203, 375-387.
[16] M. S. Dennis, M. Zhang, Y. G. Meng, M. Kadkhodayan, D. Kirchhofer, D. Combs, L. A. Damico, *J. Biol. Chem.* 2002, 277, 35035-35043.
[17] M. F. T. Koehler, K. Zobel, M. H. Beresini, L. D. Caris, D. Combs, B. D. Paasch, R. A. Lazarus, *Bioorg. Med. Chem. Lett.* 2002, 12, 2883-2886.
[18] K. Zobel, M. F. T. Koehler, M. H. Beresini, L. D. Caris, D. Combs, *Bioorg. Med. Chem. Lett.* 2003, 13, 1513-1515.
[19] C. E. Dumelin, S. Triissel, F. Buller, E. Trachsel, F. Bootz, Y. Zhang, L. Mannocci, S. C. Beck, M. Drumea-Mirancea, M. W. Seeliger, et al., *Angew. Chem. Int. Ed. Engl.* 2008, 47, 3196-201.
[20] H. Qu, P. Magotti, D. Ricklin, J. D. Lambris, in *Proc. Twenty-First Am. Pept. Symp.* (Ed.: M. Lebl), Prompt Scientific Publishing, Bloomington, Ind., 2009, pp. 219-220.
[21] R. B. Lauffer, D. J. Parmelee, S. U. Dunham, H. S. Ouellet, R. P. Dolan, S. Witte, T. J. McMurry, R. C. Walovitch, *Radiology* 1998, 207, 529-538.
[22] B. J. C. Janssen, E. F. Halff, J. D. Lambris, P. Gros, *J. Biol. Chem.* 2007, 282, 29241-29247.
[23] P. Magotti, D. Ricklin, H. Qu, Y.-Q. Wu, Y. N. Kaznessis, J. D. Lambris, *J. Mol. Recognit.* 2009, 22, 495-505.

[24] R. Karlsson, P. S. Katsamba, H. Nordin, E. Pol, D. G. Myszka, *Anal. Biochem.* 2006, 349, 136-147.
[25] M. Katragadda, P. Magotti, G. Sfyroera, J. D. Lambris, *J. Med. Chem.* 2006, 49, 4616-4622.
[26] R. N. Muller, B. Radüchel, S. Laurent, J. Platzek, C. Pierart, P. Mareski, L. Vander Elst, *Eur. J. Inorg. Chem.* 1999, 1949-1955.
[27] P. Caravan, N. J. Cloutier, M. T. Greenfield, S. A. McDermid, S. U. Dunham, J. W. M. Bulte, J. C. Amedio, R. J. Looby, R. M. Supkowski, W. D. Horrocks, et al., *J. Am. Chem. Soc.* 2002, 124, 3152-3162.
[28] J. Ghuman, P. A. Zunszain, I. Petitpas, A. A. Bhattacharya, M. Otagiri, S. Curry, *J Mol Riot* 2005, 353, 38-52.
[29] L. Aarons, D. M. Grennan, M. Siddiqui, *Eur. J. Clin. Pharmacol.* 1983, 25, 815-818.
[30] N. J. Waters, R. Jones, G. Williams, B. Sohal, *J. Pharm. Sci.* 2008, 97, 4586-4595.

The present invention is not limited to the embodiments described and exemplified above, but is capable of variation and modification within the scope of the appended claims.

What is claimed:

1. A method of producing one or more selected modified compstatin analogs, comprising:

(a) providing a compstatin analog comprising a peptide having a sequence of SEQ ID NO:6, which is:

Xaa1-Cys-Val-Xaa2-Gln-Xaa3-Xaa4-Gly-Xaa5-His-Xaa6-Cys-Xaa7 (SEQ ID NO:6), in which Gly between Xaa4 and Xaa5 is N-methylated to constrain the backbone conformation;

wherein:

Xaa1 is Ile or Gly;

Xaa2 is Trp or an analog of Trp, wherein the analog of Trp has increased hydrophobic character as compared with Trp;

Xaa3 is Asp or Asn;

Xaa4 is Trp or an analog of Trp comprising a chemical modification to its indole ring wherein the chemical modification increases the hydrogen bond potential of the indole ring;

Xaa5 is His, Ala, Phe or Trp;

Xaa6 is Arg or Orn; and

Xaa7 is Thr, Ile, Leu, Nle, N-methyl Thr or N-methyl Ile, wherein a carboxy terminal —OH of any of the Thr, Ile, Leu, Nle, N-methyl Thr or N-methyl Ile optionally is replaced by —$NH_2$, and the peptide is cyclic via a Cys-Cys or thioether bond;

(b) modifying a plurality of the compstatin analogs by adding an N-terminal component to each analog that interacts with C3, C3b or C3c in a shallow groove formed by macroglobulin domain 4 of the C3 β-chain;

(c) testing the modified compstatin analogs for interaction between the added N-terminal components thereof and a lysine residue in C3, C3b or C3c at position 386 of a C3c sequence comprising SEQ ID NO:5, or equivalent residue thereof on an equivalent sequence of C3, C3b or C3c; and (d) selecting the modified compstatin analogs having N-terminal components that interact with the lysine residue in C3, C3b or C3c at position 386 of a C3c sequence comprising SEQ ID NO:5, or equivalent residue thereof on an equivalent sequence of C3, C3b or C3c; thereby producing the one or more selected modified compstatin analogs.

2. The method of claim 1, further comprising comparing binding affinity for C3, C3b or C3c of the selected modified compstatin analogs with that of analog ABM2-Cp20 for C3, C3b or C3c.

3. The method of claim 1, further comprising testing the selected modified compstatin analogs for binding to albumin.

* * * * *

SEQUENCE LISTING

```
<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: DISULFID
<222> LOCATION: (2)..(12)

<400> SEQUENCE: 1

Ile Cys Val Val Gln Asp Trp Gly His His Arg Cys Thr
1               5                   10

<210> SEQ ID NO 2
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (13)..(13)
<223> OTHER INFORMATION: METHYLATION
<220> FEATURE:
<221> NAME/KEY: MOD_RES
<222> LOCATION: (13)..(13)
<223> OTHER INFORMATION: AMIDATION

<400> SEQUENCE: 2

Ile Cys Val Trp Gln Asp Trp Gly Ala His Arg Cys Ile
1               5                   10

<210> SEQ ID NO 3
<211> LENGTH: 14
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: D-Tyr
```

-continued

```
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 3

Tyr Ile Cys Val Trp Gln Asp Trp Gly Ala His Arg Cys Ile
1               5                   10

<210> SEQ ID NO 4
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: Joined to ABM2 by amide linkage
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (13)..(13)
<223> OTHER INFORMATION: METHYLATION
<220> FEATURE:
<221> NAME/KEY: MOD_RES
<222> LOCATION: (13)..(13)
<223> OTHER INFORMATION: AMIDATION

<400> SEQUENCE: 4

Ile Cys Val Trp Gln Asp Trp Gly Ala His Arg Cys Ile
1               5                   10

<210> SEQ ID NO 5
<211> LENGTH: 643
<212> TYPE: PRT
<213> ORGANISM: Homo sapiens

<400> SEQUENCE: 5

Ser Pro Met Tyr Ser Ile Ile Thr Pro Asn Ile Leu Arg Leu Glu Ser
1               5                   10                  15

Glu Glu Thr Met Val Leu Glu Ala His Asp Ala Gln Gly Asp Val Pro
                20                  25                  30

Val Thr Val Thr Val His Asp Phe Pro Gly Lys Lys Leu Val Leu Ser
            35                  40                  45

Ser Glu Lys Thr Val Leu Thr Pro Ala Thr Asn His Met Gly Asn Val
```

```
                    50                  55                  60
Thr Phe Thr Ile Pro Ala Asn Arg Glu Phe Lys Ser Glu Lys Gly Arg
 65                  70                  75                  80

Asn Lys Phe Val Thr Val Gln Ala Thr Phe Gly Thr Gln Val Val Glu
                     85                  90                  95

Lys Val Val Leu Val Ser Leu Gln Ser Gly Tyr Leu Phe Ile Gln Thr
                    100                 105                 110

Asp Lys Thr Ile Tyr Thr Pro Gly Ser Thr Val Leu Tyr Arg Ile Phe
                    115                 120                 125

Thr Val Asn His Lys Leu Leu Pro Val Gly Arg Thr Val Met Val Asn
                    130                 135                 140

Ile Glu Asn Pro Glu Gly Ile Pro Val Lys Gln Asp Ser Leu Ser Ser
145                 150                 155                 160

Gln Asn Gln Leu Gly Val Leu Pro Leu Ser Trp Asp Ile Pro Glu Leu
                    165                 170                 175

Val Asn Met Gly Gln Trp Lys Ile Arg Ala Tyr Tyr Glu Asn Ser Pro
                    180                 185                 190

Gln Gln Val Phe Ser Thr Glu Phe Glu Val Lys Glu Tyr Val Leu Pro
                    195                 200                 205

Ser Phe Glu Val Ile Val Glu Pro Thr Glu Lys Phe Tyr Tyr Ile Tyr
210                 215                 220

Asn Glu Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly
                    245                 250                 255

Glu Gln Arg Ile Ser Leu Pro Glu Ser Leu Lys Arg Ile Pro Ile Glu
                    260                 265                 270

Asp Gly Ser Gly Glu Val Val Leu Ser Arg Lys Val Leu Leu Asp Gly
                    275                 280                 285

Val Gln Asn Leu Arg Ala Glu Asp Leu Val Gly Lys Ser Leu Tyr Val
                    290                 295                 300

Ser Ala Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
                    325                 330                 335

Lys Thr Pro Lys Tyr Phe Lys Pro Gly Met Pro Phe Asp Leu Met Val
                    340                 345                 350

Phe Val Thr Asn Pro Asp Gly Ser Pro Ala Tyr Arg Val Pro Val Ala
                    355                 360                 365

Val Gln Gly Glu Asp Thr Val Gln Ser Leu Thr Gln Gly Asp Gly Val
                    370                 375                 380

Ala Lys Leu Ser Ile Asn Thr His Pro Ser Gln Lys Pro Leu Ser Ile
385                 390                 395                 400

Thr Val Arg Thr Lys Lys Gln Glu Leu Ser Glu Ala Glu Gln Ala Thr
                    405                 410                 415

Arg Thr Met Gln Ala Leu Pro Tyr Ser Thr Val Gly Asn Ser Asn Asn
                    420                 425                 430

Tyr Leu His Leu Ser Val Leu Arg Thr Glu Leu Arg Pro Gly Glu Thr
                    435                 440                 445

Leu Asn Val Asn Phe Leu Leu Arg Met Asp Arg Ala His Glu Ala Lys
                    450                 455                 460

Ile Arg Tyr Tyr Thr Tyr Leu Ile Met Asn Lys Gly Arg Leu Leu Lys
465                 470                 475                 480
```

```
Ala Gly Arg Gln Val Arg Glu Pro Gly Gln Asp Leu Val Val Leu Pro
            485                 490                 495

Leu Ser Ile Thr Thr Asp Phe Ile Pro Ser Phe Arg Leu Val Ala Tyr
            500                 505                 510

Tyr Thr Leu Ile Gly Ala Ser Gly Gln Arg Glu Val Val Ala Asp Ser
            515                 520                 525

Val Trp Val Asp Val Lys Asp Ser Cys Val Gly Ser Leu Val Val Lys
530                 535                 540

Ser Gly Gln Ser Glu Asp Arg Gln Pro Val Pro Gly Gln Gln Met Thr
545                 550                 555                 560

Leu Lys Ile Glu Gly Asp His Gly Ala Arg Val Val Leu Val Ala Val
            565                 570                 575

Asp Lys Gly Val Phe Val Leu Asn Lys Lys Asn Lys Leu Thr Gln Ser
            580                 585                 590

Lys Ile Trp Asp Val Val Glu Lys Ala Asp Ile Gly Cys Thr Pro Gly
            595                 600                 605

Ser Gly Lys Asp Tyr Ala Gly Val Phe Ser Asp Ala Gly Leu Thr Phe
            610                 615                 620

Thr Ser Ser Ser Gly Gln Gln Thr Ala Gln Arg Ala Glu Leu Gln Cys
625                 630                 635                 640

Pro Gln Pro

<210> SEQ ID NO 6
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Ile or Gly
<220> FEATURE:
<221> NAME/KEY: DISULFID
<222> LOCATION: (2)..(12)
<220> FEATURE:
<221> NAME/KEY: VARIANT
<222> LOCATION: (4)..(4)
<223> OTHER INFORMATION: Xaa is Trp or an analog of Trp
<220> FEATURE:
<221> NAME/KEY: VARIANT
<222> LOCATION: (6)..(6)
<223> OTHER INFORMATION: Xaa is Asp or Asn
<220> FEATURE:
<221> NAME/KEY: VARIANT
<222> LOCATION: (7)..(7)
<223> OTHER INFORMATION: Xaa is Trp or an analog of Trp
<220> FEATURE:
<221> NAME/KEY: MOD_RES
<222> LOCATION: (8)..(8)
<223> OTHER INFORMATION: METHYLATION (optional)
<220> FEATURE:
<221> NAME/KEY: VARIANT
<222> LOCATION: (9)..(9)
<223> OTHER INFORMATION: Xaa is His, Ala, Phe or Trp
<220> FEATURE:
<221> NAME/KEY: VARIANT
<222> LOCATION: (11)..(11)
<223> OTHER INFORMATION: Xaa is Arg or Orn
<220> FEATURE:
<221> NAME/KEY: VARIANT
<222> LOCATION: (13)..(13)
<223> OTHER INFORMATION: Xaa is Thr, Ile, Leu, Nle, N-methyl Thr or N-
      methyl Ile
<220> FEATURE:
<221> NAME/KEY: MOD_RES
<222> LOCATION: (13)..(13)
```

-continued

```
<223> OTHER INFORMATION: AMIDATION (optional)

<400> SEQUENCE: 6

Xaa Cys Val Xaa Gln Xaa Xaa Gly Xaa His Xaa Cys Xaa
1               5                   10
```